(12) United States Patent
Masson

(10) Patent No.: US 8,628,849 B2
(45) Date of Patent: Jan. 14, 2014

(54) METHOD FOR PREPARING PURIFIED PYROCATECHOL

(75) Inventor: Jean-Claude Masson, Lyons (FR)

(73) Assignee: Rhodia Operations, Aubervilliers (FR)

( * ) Notice: Subject to any disclaimer, the term of this patent is extended or adjusted under 35 U.S.C. 154(b) by 582 days.

(21) Appl. No.: 12/809,318

(22) PCT Filed: Dec. 17, 2008

(86) PCT No.: PCT/EP2008/067723

§ 371 (c)(1),
(2), (4) Date: Oct. 1, 2010

(87) PCT Pub. No.: WO2009/077556

PCT Pub. Date: Jun. 25, 2009

(65) Prior Publication Data

US 2011/0064950 A1    Mar. 17, 2011

(30) Foreign Application Priority Data

Dec. 19, 2007   (FR) ...................... 07 08869

(51) Int. Cl.
*B32B 5/16*   (2006.01)

(52) U.S. Cl.
USPC ............ 428/402; 203/64; 568/749; 568/750; 568/751; 568/753

(58) Field of Classification Search
USPC ............ 428/402; 203/64; 568/749, 750, 751, 568/753
See application file for complete search history.

(56) References Cited

U.S. PATENT DOCUMENTS 5,679,223 A * 10/1997 Duncan et al. ................. 203/64

FOREIGN PATENT DOCUMENTS

| FR | 2071464 | 12/1969 |
|----|---------|---------|
| FR | 2114548 | 6/1972 |
| FR | 2121000 | 7/1972 |
| FR | 2489816 | 3/1982 |
| FR | 2856681 | 6/2003 |
| SU | 1502559 | 8/1989 |
| WO | WO 0023185 | 4/2000 |
| WO | WO 0023377 | 4/2000 |

OTHER PUBLICATIONS

Fujita et al.; "On the Reaction of Safrole, Isosafrole or 3, 4-Methylenedioxycinnamic Acid With Anilline Hydrochloride"; XP009107033; Nippon Kagaku Kaishi, 1 No. 1, 1974, pp. 127-131.
Fittig; Mager Chemische Berichte; XP002499255; No. 8, 1875, pp. 357-369.
Hamamoto et al; "*Ullmann's Encyclopedia of Industrial Chemistry*" [Online]. XP002499590; Jun. 15, 2000; Wiley-VCH Verlag GmbH & Co. KGaA.
Brown; "*The Crystal Structure of Catechol*"; XP002499589; Acta Cryst., No. 21, 1966, pp. 170-174.

* cited by examiner

*Primary Examiner* — Leszek Kiliman
(74) *Attorney, Agent, or Firm* — Hunton & Williams LLP

(57) ABSTRACT

The subject of the present invention is a method for preparing pyrocatechol from which the impurities resulting from the method for the preparation thereof have been removed. The method for preparing purified pyrocatechol from a crude pyrocatechol containing essentially pyrocatechol, small amounts of impurities including dihydroxybenzoquinone, and traces of hydroquinone and of phenolic compounds, is characterized in that it comprises at least the following steps: dissolution of the crude pyrocatechol in water, crystallization of the pyrocatechol, separation of the purified pyrocatechol and, optionally, a step of drying the purified pyrocatechol. The method of the invention may include other steps and, depending on the embodiment chosen, that may comprise a different series of steps, it is possible to obtain pyrocatechol with various degrees of purity.

32 Claims, 11 Drawing Sheets

METHOD FOR PREPARING PURIFIED PYROCATECHOL

CROSS-REFERENCE TO RELATED APPLICATIONS

This application is the U.S. National Phase of International Application Number PCT/EP2008/067723 filed on Dec. 17, 2008, which claims priority to French Application No. FR 07/08,869 filed Dec. 19, 2007.

The present invention relates to a process for preparing purified pyrocatechol.

The invention is directed toward providing pyrocatechol freed of impurities resulting from its preparation process.

According to one embodiment, the invention provides a process for obtaining pyrocatechol of high purity.

Pyrocatechol (or 1,2-dihydroxybenzene) is a product that is widely used in many fields of application as a polymerization inhibitor or antioxidant in elastomers, olefins, polyolefins or polyurethane, or as a tanning agent.

On account of its complexing properties, pyrocatechol is also used as a chelating agent and as a corrosion inhibitor.

It also serves as an intermediate in many syntheses, especially those of fragrances, cosmetics, medicaments and pesticides.

A different purity is required according to the market under consideration.

Certain fields of application, for example electronics, require products of very high purity.

There is thus a strong demand on the market for extremely pure products.

It is not easy to obtain such products at the industrial scale since the removal of a small amount of impurities is difficult.

Pyrocatechol is essentially available on the market in the form of flakes.

Admittedly, the handling of flakes is easier than that of a powder, but certain applications favor pyrocatechol in powder form, on account of the improved dissolution properties.

There is thus a demand in the market for diversified products.

One of the routes for synthesizing pyrocatechol consists in hydroxylating phenol with hydrogen peroxide, especially in the presence of homogeneous or heterogeneous acid catalysts.

Thus, as in FR 2 071 464, use may be made of a strong protic acid, i.e. an acid with a pKa in water of less than 0.1 and preferably less than −1.

As examples of strong protic acids, mention may be made, inter alia, of sulfuric acid, chlorosulfuric acid, perchloric acid, sulfonic acids, for instance methanesulfonic acid, trifluoromethanesulfonic acid, toluenesulfonic acid or phenolsulfonic acid.

As other examples of protic acid catalysts, mention may be made of sulfonic resins and more particularly the resins sold under various trade names. Mention may be made, inter alia, of the following resins: Temex 50, Amberlyst 15, Amberlyst 35, Amberlyst 36 and Dowex 50W.

The abovementioned resins are formed from a polystyrene backbone bearing functional groups that are sulfonic groups. The polystyrene backbone is obtained by polymerization of styrene and divinylbenzene, under the influence of an activation catalyst, usually an organic peroxide, which leads to a crosslinked polystyrene that is then treated with concentrated sulfuric or chlorosulfuric acid, leading to a sulfonated styrene-divinylbenzene copolymer.

It is also possible to make use of sulfonic resins, which are phenol-formaldehyde copolymers bearing on the aromatic nucleus a methylenesulfonic group, for example the resin sold under the name Duolite Arc 9359.

Other commercially available resins are also suitable for use, and mention may be made of perfluoro resins bearing sulfonic groups, and more particularly Nafion, which is a copolymer of tetrafluoroethylene and of perfluoro[2-(fluorosulfonylethoxy)propyl]vinyl ether.

As other catalysts that are suitable for use in the hydroxylation processes, mention may be made of iron II and copper II complexes (FR 2 121 000 and USSR 1 502 559) and any other catalyst of Fenton type.

Other pyrocatechol preparation processes make use of heterogeneous catalysis. Thus, it is possible to use an acidic zeolite of titanium silicalite (or titanosilicalite-1) or iron silicalite type, of the type TS-1 (FR 2 489 816), a zeolite of MEL titanium silicalite type (EP 1 131 264) or a titanozeosilite of MFI type (EP 1 123 159). It is also possible to use an MCM-22 zeolite (FR 2 856 681).

After such hydroxylation reactions, a mixture essentially comprising pyrocatechol and hydroquinone (or 1,4-dihydroxybenzene) is obtained, in variable proportions generally with a pyrocatechol/hydroquinone mass ratio of about 0.25 to 4.0, and also various by-products in much smaller amounts, especially resorcinol (or 1,3-dihydroxybenzene) and pyrogallol (or 1,2,3-trihydroxybenzene), generally in contents of about 0.5% to 4.0% by mass, these percentages being expressed relative to the amount of hydroquinone and of pyrocatechol formed.

Mixtures of variable compositions comprising, by mass, from 20% to 80% of pyrocatechol, from 80% to 20% of hydroquinone, from 0.1% to 2% of resorcinol and from 0.1% to 2% of pyrogallol are obtained.

Typically, mixtures comprising, by mass, from 50% to 80% of pyrocatechol, from 20% to 50% of hydroquinone, from 0.1% to 2% of resorcinol and from 0.1% to 2% of pyrogallol are obtained.

To isolate the pyrocatechol from crude mixtures of this type, a currently known method consists in distilling said mixture, to obtain pyrocatechol at the distillation head (which is the most volatile compound of the mixture) and at the distillation tail a mixture essentially comprising hydroquinone combined with small amounts of impurities, especially resorcinol and pyrogallol.

The distillate collected is known as "crude pyrocatechol".

The invention proposes a process that may be performed at the industrial scale making it possible, starting with crude pyrocatechol, to obtain a pyrocatechol having the desired purity.

Thus, the object of the invention is to propose a flexible process that can control the desired purity of pyrocatechol and obtain a product that satisfies requirements of high purity.

Another object of the present invention is to provide a pyrocatechol in the form of a crystalline powder having improved physicochemical characteristics especially in terms of flowability.

Another object of the invention is to provide a pyrocatechol in the form of a crystalline powder that may have various degrees of purity up to an extremely high purity.

In accordance with the process of the invention and according to the chosen embodiment, which may comprise a different sequence of steps, it is possible to modulate the purity of the product obtained.

A process has now been found, and it is this that forms the subject of the present invention, for preparing purified pyrocatechol from a crude pyrocatechol essentially containing pyrocatechol, small amounts of impurities including dihydroxybenzoquinone, traces of hydroquinone and phenolic compounds in a content of less than 5% by mass, characterized in that it comprises at least the following steps:

dissolution of the crude pyrocatechol in the water used in an amount such that the concentration of the pyrocatechol in the water is between 40% and 90% by mass, crystallization of the pyrocatechol, by cooling to a temperature of between 0 and 20° C., solid/liquid separation for separating the crystalline pyrocatechol from an aqueous phase formed from the crystallization mother liquors, and optionally a step of drying the purified pyrocatechol.

The process of the invention makes it possible to obtain, from a crude pyrocatechol that is already very clean, generally containing less than 5% (preferably less than 2.5% by mass) of impurities, to reach an extremely high purity that may be more than 99% and preferably between 99% and 99.995% by mass, and to do so with a purification yield that may be high and may exceed 90% by mass.

Thus, the process of the invention proposes the purification of pyrocatechol according to an embodiment that may be performed at the industrial scale, using as crystallization solvent in solution, exclusively water, to achieve the desired purity, which is particularly advantageous when compared with the use of an organic solvent, from an economic and environmental point of view.

Yasuji Fujita et al. described in an article [Nippon Kagaku Kaishi, 1974, No. 1, p. 127-131] the reaction of safrole, isosafrole or 3,4-methylenedioxycinnamic acid with aniline hydrochloride, which leads to the formation of various products: pyrocatechol, methylenedioxybenzene, p-toluidine, p-propylaniline, p-ethylaniline, o-propylaniline, 2-methyl-2, 3-dihydroindole. The reaction is performed at the scale of a few grams and it is mentioned in said article that the pyrocatechol is recrystallized from water.

Thus, the article discloses that pyrocatechol may be extracted with water using a reaction medium having a quite specific composition associated with the reaction under consideration. However, it does not propose a process for purifying pyrocatechol having a low content of impurities that are of different nature from the compounds mentioned in said article and that are in different proportions.

It cannot in any way be deduced from said article that it is possible at the industrial scale to purify pyrocatechol using only water to achieve purities that may be extremely high.

A process for purifying pyrocatechol performed in water has never been described hitherto, for the reason that pyrocatechol is of very high solubility in water, for example at 20° C., 31.2 g/100 g of solution and at 100° C. 98.2 g/100 g of solution [Ullmann's Encyclopedia of Industrial Chemistry].

Usually, a person skilled in the art purifies a product by performing a crystallization in solution in a solvent in which the product to be purified is sparingly soluble at the crystallization end temperature and usually an aromatic hydrocarbon, benzene or toluene, is recommended as solvent from which pyrocatechol is recrystallized.

Going against the usual practice of a person skilled in the art, the Applicant proposes a process for purifying pyrocatechol performed in water, the process being able to be performed at the industrial scale, according to various embodiments.

By means of controlling the process parameters, especially the concentration and the crystallization end temperature, the process of the invention makes it possible to obtain a very pure pyrocatechol with a very good purification yield, preferably of greater than 90% by mass.

Thus, according to the invention, a pyrocatechol is obtained whose purity is more or less improved according to the type of embodiment of the invention.

The composition of the crude pyrocatechol $PC^0$ treated according to the steps of the process of the invention may vary within a quite wide range, the process of the invention however proving to be most especially advantageous for crude pyrocatechols essentially containing pyrocatechol in a proportion of at least 97.5% by mass (preferably of at least 99%) and small amounts of impurities of less than 2.5% by mass (preferably less than 1%). The major impurity is dihydroxybenzoquinone, and traces of hydroquinone and of phenolic compounds are present.

The concentration of the various impurities is given as a guide.

The ratio between the mass of dihydroxybenzoquinone and the mass of the sum of the impurities generally ranges between 0.5 and 0.8.

The ratio between the mass of the phenolic compounds and the mass of the sum of the impurities usually ranges between 0.18 and 0.4.

The ratio between the mass of hydroquinone and the mass of the sum of the impurities ranges between 0.02 and 0.10.

The process of the invention is particularly advantageous for treating crude pyrocatechols comprising pyrocatechol in a proportion of from 97.5% to 99.9% by mass, and contents of impurities of about from 0.1% to 2.5% by mass and especially from 1% to 2% by mass relative to the total mass of the crude pyrocatechol.

However, the invention may also apply to crude pyrocatechols that are richer in impurities, beyond 2.5% impurities, which may be up to 5% by mass.

According to one particular embodiment, the crude pyrocatechol $PC^0$ treated according to the process of the invention is obtained, or may be obtained, from a reaction mixture derived from a hydroxylation of phenol with hydrogen peroxide in the presence of acid catalysts of the type mentioned hereinabove in the present description, followed by a distillation for recovering the crude pyrocatechol at the head.

A crude pyrocatechol $PC^0$ that is particularly suitable for use in the process of the invention comprises, by mass relative to the total amount of crude pyrocatechol:

from 97.5% to 99.9% of pyrocatechol,
from 0.003% to 0.07% of hydroquinone,
from 0.02% to 0.5% of phenolic compounds,
from 0.07% to 1.5% of dihydroxybenzoquinone.

In the present invention, the term "pyrocatechol" means 1,2-dihydroxybenzene (CAS RN 120-80-9) with a melting point of 103° C.±1° C., "hydroquinone" means 1,4-dihydroxybenzene (CAS RN 123-31-9) with a melting point of 172° C.±1° C., dihydroxybenzoquinone (CAS RN 615-94-1), phenol (CAS RN 108-95-2) with a melting point of 40.9±1° C. Melting points are especially indicated in "Ullmann's Encyclopedia of Industrial Chemistry (2004), 7th edition, Wiley VCH (electronic version)".

Irrespective of the exact nature of the crude pyrocatechol $PC^0$ treated according to the process of the invention, the steps of the process of the invention are advantageously performed under the conditions outlined hereinbelow.

In order to facilitate understanding of the process of the invention, FIGS. 1 to 8 that represent schematically the different variants of the process of the invention are given below, without, however, limiting the scope of the invention thereto.

FIG. 1

In accordance with the process of the invention, dissolution of pyrocatechol in water is first performed, followed by crystallization, solid/liquid separation and drying.

More specifically, the process comprises the following steps:
- dissolution of the crude pyrocatechol in water,
- crystallization of the pyrocatechol,
- solid/liquid separation for separating the crystalline pyrocatechol from an aqueous phase formed from the crystallization mother liquors ($F_1$),
- drying of the pyrocatechol with removal of water ($F_2$).

The latter step is optional but, generally, pyrocatechol is sold in a dry form.

The pyrocatechol and the water are introduced into a stirred reactor whose temperature may be controlled either using a heat exchanger or by circulating a heat-exchange fluid in a jacket with which it is equipped.

As heat-exchange fluids that are suitable for use in the invention, mention may be made especially of water or an organic solvent chosen from heavy esters of carboxylic acids (for example octyl phthalate), aromatic ethers, for instance diphenyl ether and/or benzyl ether, biphenyl, terphenyls, other polyphenyls that are optionally partially hydrogenated, paraffinic and/or naphthenic oils, petroleum distillation residues, etc.

The amount of water introduced to perform the dissolution of the pyrocatechol is such that the concentration of the pyrocatechol in water is between 40% and 90% by mass and preferably between 50% and 70% by mass.

Advantageously, demineralized or distilled water is used in the process of the invention.

The dissolution operation is preferably performed at a temperature ranging from 40° C. to 100° C.

The various parameters are adjustable and the concentration may be proportionately higher the higher the chosen temperature.

In a following step, crystallization of the pyrocatechol is performed by cooling from the dissolution temperature to a lower temperature of between 0 and 20° C. and preferably between 0 and 10° C.

The crystallization is performed in conventionally used apparatus such as stirred reactors (known as crystallizing basins) with internal exchangers and/or circulation of a heat-exchange fluid in a jacket. The cooling may also be performed by partial evaporation of the solvent (water) under reduced pressure (between 15 mbar and 250 mbar) and optionally with recycling of the condensates.

The operation generally lasts for between 120 and 600 minutes and depends on the mode of crystallization, the size of the crystallizing basins and the feed charges or streams.

According to a continuous mode, the residence time, expressed as the ratio between the working volume of the reactor and the volume output of the feed stream, generally ranges between 30 minutes and 6 hours and preferably between 2 and 4 hours.

The stirring is defined by the dissipated power, which is preferably between 0.4 and 1.2 kwatt/m$^3$ of reactor volume.

It is also possible to control the particle size of the product obtained by introducing crystallization seeds in a content preferably of less than 2% expressed relative to the mass of pyrocatechol crystals to be obtained. The preferred content is between 0.5% and 1% by mass. As crystallization seeds, it is possible to use a small amount of crystalline pyrocatechol originating from a preceding manufacture and of suitable particle size.

The crystal size and distribution are controlled by especially varying the following parameters: initial concentration of the crude pyrocatechol, cooling temperature profile, seeding, stirring power and residence time in the crystallizing basin.

At the end of the operation, a suspension of pyrocatechol crystals is obtained.

Separation of the crystalline product is then performed according to standard solid/liquid separation techniques, preferably by filtration, centrifugation or draining.

The separation is generally performed at the crystallization end temperature, but a different temperature may be chosen.

A solid is recovered, which is essentially wet purified pyrocatechol comprising from 3% to 20% and preferably from 3% to 10% of water, depending on the separation technique used, and also an aqueous phase formed from the crystallization mother liquors ($F_1$) essentially comprising water, pyrocatechol in a content usually of less than about 25% and preferably greater than or equal to 10% by mass.

The moisture content is determined according to the general method of Karl Fischer (ISO standard 760—1978) on a machine of Metrohm 758 type.

It should be noted that the dissolution and crystallization operations may be performed in continuous or batch mode.

According to a continuous embodiment, a cascade of reactors and of stirred crystallizing basins in series or in parallel with temperatures that may be different but chosen in the predefined zone may be provided.

As mentioned previously, it is possible to subject the recovered pyrocatechol to a drying operation.

The drying temperature is advantageously chosen between 50° C. and 100° C. and preferably between 50° C. and 70° C.

The drying is performed according to the usual techniques known to those skilled in the art and in conventionally used apparatus such as contact dryers at atmospheric pressure or under reduced pressure, convection dryers with air or oxygen-depleted air (such as a pneumatic dryer) or an inert gas, preferably nitrogen, with the possibility of recycling the inert gas. The pyrocatechol may also be dried according to the fluidized bed technique in air, oxygen-depleted air or nitrogen with the possibility of recycling the inert gas.

The drying is performed in particular using a drying machine in a Retsch fluidized bed.

After drying, a stream ($F_2$) is obtained, formed essentially of water and the dried product, namely pyrocatechol $PC^1$, whose chemical characteristics are as follows:
- the pyrocatechol content is greater than or equal to 99.8%,
- the hydroquinone content is less than 10 ppm,
- the dihydroxybenzoquinone content is less than 40 ppm,
- the content of phenolic compounds is less than 40 ppm.

The contents of organic impurities are determined by high performance liquid chromatography. They are expressed relative to a dry product.

According to the embodiment in FIG. 1, the pyrocatechol content obtained is less than or equal to 99.99% approximately when the purity of the crude pyrocatechol is the lowest.

Thus, higher purities may also be obtained.

According to this embodiment, a purification yield of greater than or equal to 90% by mass may be obtained by selecting an initial concentration of the crude pyrocatechol in water, within the high concentration range, preferably between 50% and 90%, and a crystallization end temperature of less than or equal to 15° C. and preferably between 0° C. and 10° C.

In accordance with the process of the invention, the pyrocatechol crystals obtained have a mass per unit volume that is higher than in the case of flakes.

The apparent mass per unit volume $\rho_{nt}$ (non-tamped) of the crystals is preferably at least 0.6 g/cm$^3$ and is even more preferentially between 0.61 and 0.66 g/cm$^3$.

The apparent mass per unit volume $\rho_t$ (tamped) of the crystals is preferably at least 0.65 g/cm³ and is more preferentially between 0.66 and 0.75 g/cm³.

The masses per unit volume are measured according to DIN standard ISO 787-11 of 30 Nov. 1982 entitled "General methods of test for pigments and extenders. Determination of tamped volume and apparent density after tamping". The Stampfvolumeter STAV 2003 machine or any equivalent machine equipped with a standardized 250 ml specimen according to standard ISO 4788 may be used, for example.

The measurement is performed on a dried pyrocatechol with a residual moisture content of the crystals of between 0.25% and 0.5% by mass and obtained after drying in a fluidized bed at 60° C. for 10 minutes.

The compressibility index $i_c$ may also be defined from the measurements of the tamped and non-tamped apparent mass per unit volume according to the equation $$i_c = (\rho_t - \rho_{nt})/\rho_t$$

in which:
$i_c$ represents the compressibility index,
$\rho_t$ represents the tamped apparent mass per unit volume in g/cm³,
$\rho_{nt}$ represents the non-tamped apparent mass per unit volume in g/cm³.

The pyrocatechol obtained according to the process of the invention has a very low compressibility index $i_c$, of less than 0.1 and preferably between 0.05 and 0.09.

As regards the crystal size, it ranges after drying between 10 and 1000 µm.

The crystal size expressed by the median diameter ($d_{0.5}$) may range between 200 µm and 500 µm, but is preferably between 250 µm and 350 µm.

The median diameter ($d_{0.5}$) is defined as being such that 50% by mass of the particles have a diameter greater or less than the median diameter.

It is pointed out that the size distribution spread is expressed by the variation coefficient (CV) below:

$$CV = (d_{0.9} - d_{0.1})/2d_{0.5}$$

$d_{0.9}$: 90% by mass of the particles have a diameter less than the diameter $d_{0.9}$,
$d_{0.5}$: 50% by mass of the particles have a diameter greater or less than the median diameter,
$d_{0.1}$: 10% by mass of the particles have a diameter less than the diameter $d_{0.1}$.

The variation coefficient of the population of crystals advantageously ranges between 0.9 and 1.1.

The particle size analysis is performed on a Malvern 2000 laser granulometer in dry mode (Scirocco dispersion of the dry particles).

The measurement is performed on a sample having the same moisture content as mentioned previously.

Another technique for measuring the particle size lies in a screening technique performed using normalized standard screens made of stainless steel (standard NFX 11-504/ISO 3310-2) using a Retsch model AS 200 laboratory screening machine at a vibration lateral amplitude of 1.5 mm.

The powder is screened through 8 screens of diameter 200 mm with a mesh size of 100 µm, 200 µm, 315 µm, 500 µm, 800 µm, 1000 µm, 2500 µm and 5000 µm.

The screening time determined experimentally is 300 seconds when an antistatic powder is present, and 450 seconds when it is absent.

An antistatic agent of the type such as silica (Aerosil or Tixosil) may be added, generally in a proportion of 0.01% by mass.

The particle size fractions obtained are weighed.
The following particle size distribution is obtained:
10% by mass of the particles have a diameter of less than 200-250 µm,
50% by mass of the particles have a diameter of less than or greater than 300-500 µm,
90% by mass of the particles have a diameter of less than 750-800 µm,
100% by mass of the particles have a diameter of less than 1000 µm.

As regards the flowability properties, this is determined using a Dietmar Schulze RST-0.1.pc automatic annular cell.

The standard used is ASTM D6773-02 Standard Shear Test Method For Bulk Solid Using The Schulze Ring Shear Tester.

A powder is considered as having excellent flowability (being free-flowing) when the flowability index $ff_c$ obtained is greater than 10 and good flowability for an index of between 4 and 10.

The product is cohesive when the index is between 2 and 4 and very cohesive for an index of between 1 and 2.

For an index of less than 1, the product is considered to have no flowability.

According to the invention, a pyrocatechol with a flowability index of greater than 15, preferably greater than or equal to 20 and even more preferentially between 20 and 25 is obtained.

FIG. 2

In accordance with the process of the invention, dissolution of the pyrocatechol in water is first performed, followed by crystallization with evaporation, solid/liquid separation and drying.

More specifically, the process comprises the following steps:
dissolution of the crude pyrocatechol in water,
crystallization of the pyrocatechol with evaporation and output of a stream of condensates ($F_3$),
solid/liquid separation allowing separation of the crystalline pyrocatechol from an aqueous phase formed from the crystallization mother liquors ($F_4$),
drying of the pyrocatechol with removal of water ($F_5$).

This embodiment is identical to that of FIG. 1, with the exception that the evaporation performed during the crystallization step makes it possible to adjust the pyrocatechol concentration and to manage the heat balance of the reaction.

The evaporation operation may be performed by heating under atmospheric pressure or under reduced pressure ranging from 25 mbar to 1 bar, for a temperature ranging from 25° C. to 100° C.

The evaporation may be performed before or during the crystallization itself in batch mode or throughout the crystallization according to a continuous mode.

The crystallization is performed as described in FIG. 1.

Following the drying, a stream ($F_5$) is obtained, formed essentially from water and the dried product, i.e. the pyrocatechol $PC^2$ whose physicochemical characteristics are similar to those of $PC^1$.

According to this embodiment, a purification yield of greater than or equal to 90% may be obtained by selecting a concentration of crude pyrocatechol in water as defined according to FIG. 1, preferably of between 50% and 90% by mass. This may be obtained by means of a concentration operation. Similarly, a low crystallization end temperature is desired.

FIG. 3

According to one variant of the process described in FIG. 1, it is possible to envision an additional step of washing performed before the drying step. However, given the high solubility of pyrocatechol, washing is not recommended on account of the loss of yield in the washing waters.

The washing is performed using a minimum amount of water representing a ratio between the mass of washing water and the mass of mother liquors constituting the moisture content of the pyrocatechol, of not more than 3 and preferably from 0.5 to 1.0.

The washing may be performed on the same solid/liquid separation apparatus; or on a filter, on a drainer or in a centrifuge.

Washing makes it possible to obtain a pyrocatechol $PC^3$ with a purity improved by a few ppm (5 to 10).

More specifically, the process of FIG. 3 comprises the following steps:
dissolution of the crude pyrocatechol in water,
crystallization of the pyrocatechol,
solid/liquid separation for separating the crystalline pyrocatechol from an aqueous phase formed from the crystallization mother liquors ($F_6$),
washing with water of the pyrocatechol separated out, to collect the washing liquors ($F_7$),
drying of the washed pyrocatechol with removal of water ($F_8$).

The dissolution of the pyrocatechol in water, the crystallization and the separation are performed as described above, but washing of the pyrocatechol separated out is then performed before an optional drying.

At the end of the operation, the washing liquors ($F_7$), predominantly comprising water and pyrocatechol and impurities in a content ranging between 10% and 25% by mass, are collected for the crystallization end temperature range of between 5 and 15° C.

The washed pyrocatechol is subjected to a drying operation as described previously, and $PC^3$ and a stream ($F_8$) formed essentially from water are obtained.

As in the process defined in FIG. 1, a purification yield of greater than or equal to 90% may be obtained by adjusting the concentration of the crude pyrocatechol in water and the crystallization end temperature.

FIG. 4

In accordance with the process of the invention, dissolution of the pyrocatechol in water is first performed, followed by crystallization with evaporation, solid/liquid separation, washing and drying.

More specifically, the process comprises the following steps:
dissolution of the crude pyrocatechol in water,
crystallization of the pyrocatechol with evaporation and output of a stream of condensates ($F_9$),
solid/liquid separation allowing the crystalline pyrocatechol to be separated from an aqueous phase formed by the crystallization mother liquors ($F_{10}$),
washing with water of the pyrocatechol separated out, allowing the washing liquors ($F_{11}$) to be collected,
drying of the washed pyrocatechol with removal of water ($F_{12}$).

This embodiment is identical to that of FIG. 3, except for the fact that the evaporation performed during the crystallization step makes it possible to adjust the pyrocatechol concentration and to manage the heat balance of the reaction.

The evaporation operation may be performed by heating at atmospheric pressure or under reduced pressure.

The evaporation may be performed before or during the crystallization itself in batch mode or throughout the crystallization according to a continuous mode.

The crystallization is performed as described in FIG. 1.

The washing is performed as described in FIG. 3.

Following the drying, a stream ($F_{12}$) is obtained, formed essentially from water and the dried product, i.e. the pyrocatechol $PC_4$, the physicochemical characteristics of which are similar to those of $PC^3$.

As in the process described in FIG. 3, a high concentration of crude pyrocatechol in water may be obtained by also modifying the concentration operation.

FIG. 5

In accordance with the process of the invention, a pyrocatechol $PC^5$ of different quality is obtained according to a process comprising the following steps:
dissolution of the crude pyrocatechol in water,
crystallization of the pyrocatechol,
solid/liquid separation for separating the crystalline pyrocatechol from an aqueous phase formed from the crystallization mother liquors ($F_{13}$),
drying of the pyrocatechol with removal of water ($F_{14}$),
recycling of the stream ($F_{13}$) after optional concentration of said stream, in the dissolution or crystallization step,
purging ($P_1$) at the outlet of the concentration step or purging ($P_2$) on the stream formed by the aqueous phase ($F_{13}$) obtained from the separation of the pyrocatechol after crystallization.

According to this variant of the process of the invention, the steps described previously are repeated and the stream ($F_{13}$) is recycled after optional concentration of said stream in the dissolution or crystallization step.

To control the pyrocatechol content in the process of the invention, it may be adjusted by concentrating the stream ($F_{13}$) by evaporating a water stream ($F_{15}$).

According to one characteristic of the process of the invention, concentration of the stream ($F_{13}$) may be performed so as to increase the pyrocatechol concentration in the stream chosen between 10% and 90% by mass and preferably between 10% and 60% by mass.

The concentration operation may be performed by heating at atmospheric pressure or under a reduced pressure at a temperature of between 70° C. and 100° C.

The pyrocatechol concentration is adjusted according to whether the stream is recycled in the dissolution step or in the crystallization step.

Thus, a stream of water ($F_{15}$) is removed during this operation.

A first mode consists, while remaining in the abovementioned temperature region, in reducing the reaction pressure, by depressurization. This depressurization is performed so as to remove at the head the required amount of water to reach in the reaction medium the target pyrocatechol concentration.

Another embodiment for concentrating the reaction medium consists in distilling the amount of some of the water to achieve in the reaction medium, the desired pyrocatechol concentration.

The distillation may be performed at atmospheric pressure at a temperature of about 100° C.

The distillation may also be performed at a pressure slightly lower than atmospheric pressure, for example from 200 to 750 mm of mercury and at a temperature below 100° C. In general, the pressure is chosen to have a distillation point of between 70° C. and 100° C.

The distillation may also be performed at a pressure higher than atmospheric pressure.

These operations are performed in standard apparatus such as distillation columns or standard evaporators at atmospheric pressure, under reduced pressure or at a pressure higher than atmospheric pressure.

This concentrated stream is advantageously recycled either into the dissolution step or into the crystallization feed.

In order to minimize the impurities present in this recirculation loop, it is preferable to perform one or more purges of one of the streams comprising the impurities.

The purge consists in removing a fraction of said stream. It is determined such that the overall loss of pyrocatechol relative to the crude pyrocatechol is preferentially between 0.5% and 2% by mass.

A purge ($P_1$) may be performed at the outlet of the concentration zone. It is performed by means of a valve placed on the pipe conveying the concentrated stream, at the outlet of the concentration operation but before recycling.

It is also possible to perform a purge ($P_2$) on the stream formed by the aqueous phase ($F_{13}$) derived from the separation of the pyrocatechol after crystallization.

It is preferable to perform the purge at the outlet of the concentration area.

The purge may be performed in continuous or batch mode.

Controlling the purge makes it possible to adjust the chemical purity of the pyrocatechol obtained and also the overall yield for the process.

Following the various operations defined according to the scheme of FIG. 5, pyrocatechol $PC^5$ is obtained, the chemical purity of which is adjusted by withdrawing a purge stream ($P_1$) after the concentration step or a purge stream ($P_2$) after the step of separating the mother liquors.

Following the drying, a stream ($F_{14}$) is obtained, formed essentially from water and the dried product, namely the pyrocatechol $PC^5$, the chemical characteristics of which are as follows:
the pyrocatechol content is greater than or equal to 99.8%,
the hydroquinone content is less than or equal to 100 ppm,
the dihydroxybenzoquinone content is less than 700 ppm,
the content of phenolic compounds is less than 300 ppm.

According to the embodiment of FIG. 5, the pyrocatechol content obtained is greater than or equal to 99.8% approximately.

The physical characteristics of the crystals, tamped or non-tamped mass per unit volume, distribution of the crystals, flowability properties, are equivalent to those of pyrocatechol obtained according to FIG. 1.

FIG. 6

In accordance with the process of the invention, a pyrocatechol $PC^6$ of quality similar to that of $PC^5$ is obtained according to a process comprising the following steps:
dissolution of the crude pyrocatechol in water,
crystallization of the pyrocatechol with evaporation and output of a stream of condensates ($F_{16}$),
solid/liquid separation allowing the crystalline pyrocatechol to be separated from an aqueous phase formed from the crystallization mother liquors ($F_{17}$),
drying of the pyrocatechol with removal of water ($F_{18}$),
recycling of the stream ($F_{17}$) after optional concentration of said stream, in the dissolution or crystallization step,
purging ($P_3$) at the outlet of the concentration step or purging ($P_4$) on the stream formed by the aqueous phase ($F_{17}$) obtained from the separation of the pyrocatechol after crystallization.

This embodiment is identical to that of FIG. 5, except for the fact that the evaporation performed during the crystallization step makes it possible to adjust the pyrocatechol concentration and to manage the heat balance of the reaction.

To control the pyrocatechol content, it may be adjusted by concentrating the stream ($F_{17}$) by evaporating a water stream ($F_{19}$).

The evaporation operation may be performed by heating at atmospheric pressure or under reduced pressure.

The evaporation may be performed before or during the crystallization itself in batch mode or throughout the crystallization in a continuous mode.

The crystallization is performed as described in FIG. 1.

Following drying, a stream ($F_{18}$) is obtained formed essentially from water and the dried product, i.e. the pyrocatechol $PC^6$, the physicochemical characteristics of which are similar to those of $PC^5$.

FIG. 7

In accordance with the process of the invention, a pyrocatechol $PC^7$ of different quality is obtained according to a process comprising the following steps:
dissolution of the crude pyrocatechol in water,
crystallization of the pyrocatechol,
solid/liquid separation allowing the crystalline pyrocatechol to be separated from an aqueous phase formed from the crystallization mother liquors ($F_{20}$),
washing with water of the pyrocatechol separated out allowing the washing liquors ($F_{21}$) to be collected,
drying of the pyrocatechol with removal of water ($F_{22}$),
recycling of the stream ($F_{20}$) after optional concentration of said stream, in the dissolution or crystallization step,
purging ($P_5$) at the outlet of the concentration step or purging ($P_6$) on the stream formed by the aqueous phase ($F_{20}$) obtained from the separation of the pyrocatechol after crystallization.

To control the pyrocatechol content, it may be adjusted by concentrating the stream ($F_{20}$) by evaporating a water stream ($F_{23}$).

According to one variant of the process of the invention, the washing liquors ($F_{21}$) may be mixed with the crystallization mother liquors ($F_{20}$) before the concentration operation.

The physical characteristics of the crystals are equivalent to those of the pyrocatechol obtained according to FIG. 1.

The purity obtained may be modified according to the degree of recycling of the crystallization liquors, optionally the washing liquors and according to the degree of purging.

FIG. 8

In accordance with the process of the invention, a pyrocatechol $PC^8$ of different quality is obtained according to a process comprising the following steps:
dissolution of the crude pyrocatechol in water,
crystallization of the pyrocatechol with evaporation and output of a stream of condensates ($F_{24}$),
solid/liquid separation allowing the crystalline pyrocatechol to be separated from an aqueous phase formed from the crystallization mother liquors ($F_{25}$),
washing with water of the pyrocatechol separated out allowing the washing liquors ($F_{26}$) to be collected,
drying of the pyrocatechol with removal of water ($F_{27}$),
recycling of the stream ($F_{25}$) after optional concentration of said stream, in the dissolution or crystallization step,
purging ($P_7$) at the outlet of the concentration step or purging ($P_8$) on the stream formed by the aqueous phase ($F_{25}$) obtained from the separation of the pyrocatechol after crystallization.

To control the pyrocatechol content, it may be adjusted by concentrating the stream ($F_{25}$) by evaporating a water stream ($F_{28}$).

According to one variant of the process of the invention, the washing liquors ($F_{26}$) may be mixed with the crystallization mother liquors ($F_{25}$) before the concentration operation.

The physical characteristics of the crystals are equivalent to those of the pyrocatechol obtained according to FIG. 1.

The purity obtained may be modified according to the degree of recycling of the crystallization liquors, optionally of the washing liquors and according to the degree of purging.

In accordance with the process of the invention, it is possible to purify the pyrocatechol obtained or that may be obtained from a reaction mixture derived from a hydroxylation of phenol with hydrogen peroxide in the presence of an acid catalyst followed by distillation of the pyrocatechol from the reaction mixture, using a sequence of steps chosen as a function of the targeted object.

Advantageously, the various operations mentioned previously, dissolution, crystallization, separation, washing/separation, drying, concentration and recycling of the streams with purging, etc. are performed under an atmosphere of inert gases, preferably under nitrogen.

It should be noted that the invention does not exclude additional steps inserted into the sequences defined by the invention, in particular the addition of a common treatment of solids, in particular a treatment with carbon black (or active charcoal), to improve the whiteness of the product obtained.

For example, according to the schemes of FIGS. 1 to 8, it is possible to perform this treatment before the crystallization operation and following the dissolution operation, by adding an amount of carbon black or of active charcoal in a proportion of from 0.02% to 0.50% relative to the mass of pyrocatechol.

This treatment is performed in a stirred reactor.

It is followed by a solid/liquid separation performed before the crystallization step, preferably a filtration to remove the carbon black advantageously followed by a washing operation.

Another embodiment for the treatment with carbon black is to use the fixed bed technique.

Thus, the stream obtained from the dissolution operation is conveyed into a fixed bed of carbon black preferably in the form of granules.

The carbon black granules are placed in a column and the stream containing the pyrocatechol generally passes countercurrentwise through the fixed bed.

This technique makes it possible to save a separation operation.

Thus, the process of the invention is particularly advantageous since it makes it possible to obtain pyrocatechol in different degrees of purity ranging between 99% and 99.995% and preferably between 99.5% and 99.99%.

The lower limits of the purities achieved by the process of the invention are less than 10 ppm for hydroquinone, 40 ppm for dihydroxybenzoquinone and 40 ppm for the phenolic compounds.

Finally, it should be pointed out that the process of the invention is advantageous from an economic point of view since the purification yield can reach 90% and preferably 95% or higher in the case of the variants with recycling of the crystallization mother liquors and the washing liquors.

A yield higher than this value may be obtained by separately treating the purges in the case of the processes of FIGS. 5 to 8 or the crystallization and washing mother liquors in the case of the processes of FIGS. 1 to 4. The treatment consists in recovering the pyrocatechol contained in these various streams, especially by crystallization.

It is pointed out that the various weight percentages given in the present text, relative to the pyrocatechol in solid form, are expressed relative to a dry product obtained after drying to constant weight.

The process of the invention leads to the production of a pyrocatechol that has its own physicochemical characteristics.

Thus, it makes it possible to obtain a pyrocatechol in crystalline form that has improved flowability properties not achieved in the prior art.

The pyrocatechol crystals are homogeneous in size and shape. The size distribution of the particles is of Gaussian type.

Its flowability index is greater than 15, preferably greater than or equal to 20 and even more preferentially between 20 and 25.

Moreover, its compressibility index is very low, less than 0.1 and preferably between 0.05 and 0.09. It follows that the powder form obtained is such that it has a low volume variation under tamping constraint, which is an advantage during prolonged storage.

The process of the invention makes it possible to obtain the purified pyrocatechol in a very good yield of greater than or equal to 90% according to the various modes described in FIGS. 1 to 8.

To obtain a good yield according to these embodiments, it is important to have a high concentration of pyrocatechol during the crystallization of the pyrocatechol.

To do this, a high initial concentration of the crude pyrocatechol may be chosen, preferably between 50% and 90% by mass and more preferentially between 50% and 70% by mass.

In the case of a less concentrated stream, as regards the stream obtained by dissolution of the pyrocatechol in water or of the mother liquors and/or washing liquor that are recycled, a concentration operation by evaporating water is necessary in order to obtain a high pyrocatechol concentration during the crystallization: this concentration is advantageous between 50% and 90% and preferably between 50% and 70%.

Thus, FIGS. 2 and 4 mention a concentration operation during the crystallization and FIGS. 5, 6, 7 and 8 indicate a concentration operation on the mother liquors and optionally on the washing liquors.

FIGS. 6 and 8 mention both a concentration operation during the crystallization and also on the mother liquors and optionally on the washing liquors.

Moreover, the yield may be improved by selecting a lower crystallization end temperature preferably of between 0° C. and 15° C. and more preferentially between 0° C. and 10° C.

Examples of implementation of the invention are given below as non-limiting illustrations.

Examples 1 to 8 refer, respectively, to FIGS. 1 to 8.

Example 9 refers to FIG. 1 and Example 10 to FIG. 2.

The purification yield is defined as being the weight ratio expressed as a mass % between the pyrocatechol obtained expressed as anhydrous product and the pyrocatechol used in the crystallization step.

EXAMPLES

Example 1

1250 g of demineralized water at room temperature and 1250 g of crude pyrocatechol whose mass % composition is as follows: 99.843% of pyrocatechol, 0.112% of dihdyroxybenzoquinone, 0.0055% of hydroquinone, 0.0385% of phenolic compounds, are respectively placed in a jacketed stirred crystallizing basin with a working volume of 2.5 liters, stirred with a three-paddle stirring rotor with axial output and a variable speed, equipped with 4 counterpaddles at 90°, fitted with a condenser and maintained under nitrogen and at a jacket temperature of 55° C.

Total dissolution of the pyrocatechol is achieved by stirring for about 30 minutes; maintenance of the temperature of the medium at 50° C. is performed for 10 minutes.

Rapid cooling over 15 minutes from 50° C. to 26° C. is then performed.

Seeding with 2 g of crystals (screen cutoff of between 125 and 160 microns) of purified pyrocatechol initiates the crystallization at 26° C.

Slow cooling at a constant speed from 26° C. to 15° C. over 4 hours is then performed.

The suspension of crystalline pyrocatechol is then filtered on a flat filter maintained at a temperature of 15° C., under nitrogen, to obtain 760.4 g of wet pyrocatechol with a moisture content of 3.1% measured by the Karl Fischer method and 1741.6 g of mother liquors ($F_1$).

The solution of mother liquors ($F_1$) is stored for subsequent treatment.

The wet pyrocatechol is dried in an oven under reduced pressure (100 mbar) and under a stream of nitrogen at 90° C., for 6 hours with removal of 23.6 g of water ($F_2$).

736.8 g of pyrocatechol $PC^1$ are isolated, the mass composition of which, determined by high-performance liquid chromatography and expressed relative to an anhydrous product, is as follows:
    pyrocatechol content: 99.992%
    dihydroxybenzoquinone content: 37 ppm
    hydroquinone content: <10 ppm
    content of phenolic compounds: 32 ppm.
The crystallization yield is 59%.

The physical characteristics of the pyrocatechol $PC^1$ are as follows:
    diameter $d_{0.1}$: 48 μm
    median diameter $d_{0.5}$: 288 μm
    diameter $d_{0.9}$: 624
    $CV=(d_{0.9}-d_{0.1})/2d_{0.5}$: 1.0
    bulk mass per unit volume: 0.664 g/cm$^3$
    tamped mass per unit volume: 0.699 g/cm$^3$
    compressibility index: 0.05
    flowability index $ff_{c.inst.}$: 20.

Example 2

1250 g of demineralized water at room temperature and 1250 g of crude pyrocatechol whose mass % composition is as follows: 99.843% of pyrocatechol, 0.112% of dihydroxybenzoquinone, 0.0055% of hydroquinone, 0.0385% of phenolic compounds, are respectively placed in a jacketed stirred crystallizing basin with a working volume of 2.5 liters, stirred with a three-paddle stirring rotor with axial output and a variable speed, equipped with 4 counterpaddles at 90°, fitted with a condenser and maintained under nitrogen and at a jacket temperature of 55° C.

Total dissolution of the pyrocatechol is achieved by stirring for about 30 minutes; maintenance of the temperature of the medium at about 50° C. is performed for 10 minutes.

Rapid cooling over 60 minutes from 50° C. to 27° C. is then performed by placing the crystallizing basin under a variable reduced pressure between 140 mbar and 35 mbar.

A fraction of condensates of 230.9 g of water vapor ($F_3$) bearing the pyrocatechol concentration at 55% by weight in the mixture is withdrawn.

The pyrocatechol crystals appear at 27° C. Seeding is not used in this example. The crystallizing basin is returned to atmospheric pressure under a cover of nitrogen.

Slow cooling at a constant rate from 27° C. to 15° C. over 4 hours is then performed.

The suspension of crystalline pyrocatechol is then filtered on a flat filter maintained at a temperature of 15° C. under nitrogen, to obtain 811.2 g of wet pyrocatechol with a moisture content of 3.0% measured by the Karl Fischer method and 1457.9 g of mother liquors ($F_4$).

The solution of mother liquors ($F_4$) is stored for subsequent treatment.

The wet pyrocatechol is dried, in an oven under reduced pressure (100 mbar) and under a stream of nitrogen, at 90° C., for 6 hours with removal of 24.3 g of water ($F_5$).

786.9 g of pyrocatechol $PC^2$ are isolated, the mass composition of which, determined by high-performance liquid chromatography and expressed relative to an anhydrous product, is as follows:
    pyrocatechol content: 99.993%
    dihydroxybenzoquinone content: 35 ppm
    hydroquinone content: <10 ppm
    content of phenolic compounds: 30 ppm
The crystallization yield is 63%.

The physical characteristics of the pyrocatechol $PC^2$ are as follows:
    diameter $d_{0.1}$: 50
    median diameter $d_{0.5}$: 295 μm
    diameter $d_{0.9}$: 650 μm
    $CV=(d_{0.9}-d_{0.1})/2d_{0.5}$: 1.02
    bulk mass per unit volume: 0.660 g/cm$^3$
    tamped mass per unit volume: 0.702 g/cm$^3$
    compressibility index: 0.06
    flowability index $ff_{c.inst.}$: 23

Example 3

1102.5 g of demineralized water at room temperature and 1347.5 g of crude pyrocatechol, the mass % composition of which is as follows: 99.50% of pyrocatechol, 0.360% of dihydroxybenzoquinone, 0.017% of hydroquinone, 0.123% of phenolic compounds, are respectively placed in a jacketed stirred crystallizing basin with a working volume of 2.5 liters, stirred with a three-paddle stirring rotor with axial output and variable speed, equipped with 4 counterpaddles at 90°, fitted with a condenser and maintained under nitrogen and at a jacket temperature of 55° C.

Total dissolution of the pyrocatechol is achieved with stirring for about 30 minutes; maintenance of the temperature of the medium at 50° C. is performed for 10 minutes.

Rapid cooling over 15 minutes from 50° C. to 32° C. is then performed.

Slow cooling at constant rate from 32° C. to 5° C. over 4 hours is then performed (wall cooling).

Crystallization of the pyrocatechol starts spontaneously at 31° C. at low supersaturation.

The suspension of crystalline pyrocatechol is then filtered on a flat filter maintained at a temperature of 5° C., under nitrogen, to obtain 1248.8 g of wet pyrocatechol with a moisture content of 2.5% measured by the Karl Fischer method and 1201.0 g of mother liquors ($F_6$).

The solution of mother liquors ($F_6$) is stored for subsequent treatment.

The wet pyrocatechol cake is washed with 93.7 g of demineralized water at 5° C. (washing proportion of 3/1 expressed as kg of washing water/kg of mother liquors impregnating the wet cake) on the filter.

After filtration, an equivalent filtrate of washing liquors ($F_7$) is recovered.

The washed wet pyrocatechol is dried in an oven under reduced pressure (100 mbar) and under a stream of nitrogen, at 90° C., for 6 hours with removal of 30.4 g of water ($F_8$).

1218.6 g of pyrocatechol $PC^3$ are isolated, the mass composition of which, determined by high-performance liquid chromatography and expressed relative to an anhydrous product, is as follows:
    pyrocatechol content: 99.996% dihydroxybenzoquinone content: 25 ppm
hydroquinone content: <2 ppm
content of phenolic compounds: 10 ppm
The crystallization yield is 91%.
The physical characteristics of the pyrocatechol $PC^3$ are as follows:
diameter $d_{0.1}$: 45 μm
median diameter $d_{0.5}$: 285 μm
diameter $d_{0.9}$: 600 μm
$CV=(d_{0.9}-d_{0.1})/2d_{0.5}$: 0.97
bulk mass per unit volume: 0.670 g/cm$^3$
tamped mass per unit volume: 0.705 g/cm$^3$
compressibility index: 0.05
flowability index $ff_{c.inst.}$: 25

Example 4

1250 g of demineralized water at room temperature and 1250 g of molten crude pyrocatechol whose mass % composition is as follows: 98.50% of pyrocatechol, 1.078% of dihydroxybenzoquinone, 0.052% of hydroquinone, 0.370% of phenolic compounds, are respectively placed in a jacketed stirred crystallizing basin with a working volume of 2.5 liters, stirred with a three-paddle stirring rotor with axial output and variable speed, equipped with 4 90° counterpaddles, fitted with a condenser and maintained under nitrogen and at a jacket temperature of 95° C.

Total dissolution of the pyrocatechol is achieved with stirring for about 10 minutes; maintenance of the temperature of the medium at about 95° C. is performed for 10 minutes.

A fraction of condensates of water vapor of 447.9 g ($F_9$) is removed, bringing the pyrocatechol concentration to 60% by weight in the mixture, by placing the crystallizing basin under a variable reduced pressure of between 1010 mbar and 750 mbar and maintaining the boiling at 95° C.

Rapid cooling over 60 minutes from 95° C. to 39° C. is then performed by combining cooling by evaporation (with total recycling of the condensates) and wall cooling.

The crystallizing basin is returned to atmospheric pressure under a cover of nitrogen at a temperature of 39° C.

Slow wall cooling is continued at a constant rate from 39° C. to 1° C. over 4 hours.

The pyrocatechol crystals appear at 37° C. Seeding is not used in this example.

The suspension of crystalline pyrocatechol is then filtered on a flat filter maintained at a temperature of 1° C., under nitrogen, to obtain 1187.6 g of wet pyrocatechol with a moisture content of 4.0% measured by the Karl Fischer method and 864.5 g of mother liquors ($F_{10}$).

The solution of mother liquors ($F_{10}$) is stored for subsequent treatment.

The wet pyrocatechol cake is washed with 142.5 g of demineralized water at 1° C. (washing proportion of 3/1 expressed as kg of washing water/kg of mother liquors impregnating the wet cake) on the filter.

After filtration, an equivalent filtrate of washing liquor ($F_{11}$) is recovered.

The wet pyrocatechol is dried in a fluidized bed (Retsch TG 100 model) equipped with Pt 100Ω 0° C. temperature probes and a relative humidity sensor (Testo 365); the fluidization gas is nitrogen, at a temperature of 60° C., for 10 to 15 minutes with removal of 46.1 g of water ($F_{12}$).

Mechanical stirring aids the start of drying of the layer to be fluidized (height ~40 mm) at the start of drying.

Drying is stopped when the product temperature stabilizes at 60° C. and when the absolute moisture content of the drying gas exiting the fluidized bed is equal to that of the drying gas entering the fluidized bed.

1141.5 g of pyrocatechol $PC^4$ are isolated, the mass composition of which, determined by high-performance liquid chromatography and expressed relative to an anhydrous product, is as follows:
pyrocatechol content: 99.979%
dihydroxybenzoquinone content: 150 ppm
hydroquinone content: <10 ppm
content of phenolic compounds: 50 ppm
The crystallization yield is 93%.
The physical characteristics of the pyrocatechol $PC^4$ are as follows:
diameter $d_{0.1}$: 65 μm
median diameter $d_{0.5}$: 295
diameter $d_{0.9}$: 675 μm
$CV=(d_{0.9}-d_{0.1})/2d_{0.5}$: 1.03
bulk mass per unit volume: 0.670 g/cm$^3$
tamped mass per unit volume: 0.707 g/cm$^3$
compressibility index: 0.05
flowability index $ff_{c.inst.}$: 21

Example 5

A sequence of tests of the type in Example 1 is performed: tests $N_{(i)}$ with $_{(i)}$=1 to 10.

The mother liquors ($F_{13}$) of test $N_{(0)}$ are recycled at 90% into the crystallizing basin feed for test $N_{(1)}$ and so on for the following tests.

The remainder of the charge for each test is the charge of crude pyrocatechol and a remainder, or a removal of water by evaporation ($F_{15}$), to maintain a pyrocatechol concentration of 60% by mass in the medium to be crystallized. The total charge of the crystallization apparatus is maintained at 2500 g.

This series of tests $N_{(1)}$ to $N_{(10)}$ simulates the achieval of a pseudostationary state of equilibrium for a continuous crystallization process with partial recycling of the mother liquors.

The conditions of test $N_{(10)}$ are described hereinbelow.

A total charge of 2500 g of constituents formed from demineralized water and mother liquors recycled from test $N_{(9)}$ at room temperature and the remainder of crude pyrocatechol whose mass % composition is as follows: 99.843% of pyrocatechol, 0.112% of dihydroxybenzoquinone, 0.0055% of hydroquinone, 0.0385% of phenolic compounds, to obtain a pyrocatechol concentration of 60% by weight, is introduced into a jacketed stirred crystallizing basin with a working volume of 2.5 liters, stirred with a three-paddle stirring rotor with axial output and variable speed, equipped with 4 90° counterpaddles, fitted with a condenser and maintained under nitrogen and at a jacket temperature of 55° C.

The overall content of impurities in the mixture to be crystallized, relative to the pyrocatechol present, is 1.5% by mass, and the corresponding pyrocatechol purity is 98.5% by mass.

Total dissolution of the pyrocatechol is achieved with stirring for about 30 minutes; maintenance of the temperature of the medium at 50° C. is performed for 10 minutes.

Rapid cooling over 15 minutes from 50° C. to 39° C. is then performed.

Seeding with 2 g of crystals (screen cutoff of between 125 and 160 microns) of purified pyrocatechol initiates the crystallization at 38° C.

Slow cooling at constant rate from 39° C. to 5° C. over 5 hours is then performed.

The suspension of crystalline pyrocatechol is then filtered on a flat filter maintained at a temperature of 5° C., with stirring, to obtain 1393.7 g of wet pyrocatechol with a moisture content of 4.9% measured by the Karl Fischer method and 1108.3 g of mother liquors ($F_{13}$).

The solution of mother liquors ($F_{13}$) is stored for subsequent treatment.

The wet pyrocatechol is dried in an oven under reduced pressure (100 mbar) and under a stream of nitrogen, at 90° C., for 6 hours with removal of 56.7 g of water ($F_{14}$).

1337.1 g of pyrocatechol $PC^5$ are isolated, the mass composition of which, determined by high-performance liquid chromatography and expressed relative to an anhydrous product, is as follows:
  pyrocatechol content: 99.892%
  dihydroxybenzoquinone content: 695 ppm
  hydroquinone content: <100 ppm
  content of phenolic compounds: 285 ppm
  The crystallization yield is 89%.
  The physical characteristics of the pyrocatechol $PC^5$ are as follows:
  diameter $d_{0.1}$: 56 μm
  median diameter $d_{0.5}$: 329 μm
  diameter $d_{0.9}$: 738 μm
  $CV = (d_{0.9} - d_{0.1})/2d_{0.5}$: 1.04
  bulk mass per unit volume: 0.647 g/cm³
  tamped mass per unit volume: 0.703 g/cm³
  compressibility index: 0.08
  flowability index $ff_{c.inst.}$: 23

Example 6

A sequence of tests of the type of those of Example 5: tests $N_{(i)}$ with $_{(i)} = 1$ to 10, is performed.

The mother liquors ($F_{17}$) from test $N_{(0)}$ are 90% recycled into the crystallizing basin feed for test $N_{(1)}$ and so on for the following tests.

The remainder of the charge for each test is the crude pyrocatechol charge and a remainder, and/or a removal of water by evaporation ($F_{19}$) to maintain a pyrocatechol concentration of 50% by mass in the medium to be crystallized.

The total charge of the crystallization apparatus is maintained at 2500 g.

This series of tests $N_{(1)}$ to $N_{(10)}$ simulates the achieval of a pseudostationary state of equilibrium for a continuous crystallization process with partial recycling of the mother liquors.

The conditions of test $N_{(10)}$ are described hereinbelow.

A total charge of 2500 g of constituents formed from demineralized water and mother liquors recycled from test $N_{(9)}$ at room temperature and the remainder of crude pyrocatechol whose mass % composition is as follows: 99.843% of pyrocatechol, 0.112% of dihydroxybenzoquinone, 0.0055% of hydroquinone, 0.0385% of phenolic compounds, to obtain a pyrocatechol concentration of 40% by weight, is introduced into a jacketed stirred crystallizing basin with a working volume of 2.5 liters, stirred with a three-paddle stirring rotor with axial output and variable speed, equipped with 4 90° counterpaddles, fitted with a condenser and maintained under nitrogen and at a jacket temperature of 55° C.

The overall content of impurities in the mixture to be crystallized, relative to the pyrocatechol present, is 2.2% by mass, and the corresponding pyrocatechol purity is 97.8% by mass.

Total dissolution of the pyrocatechol is achieved with stirring for about 30 minutes; maintenance of the temperature of the medium at 50° C. is performed for 10 minutes.

A fraction of condensates of water vapor of 500 g ($F_{16}$) is removed, bringing the pyrocatechol concentration to 50% by mass in the mixture, by placing the crystallizing basin under a variable reduced pressure between 1010 mbar and 750 mbar and maintaining the boiling at 95° C.

Rapid cooling over 60 minutes from 95° C. to 40° C. is then performed by combining cooling by evaporation (with total recycling of the condensates) and wall cooling.

The crystallizing basin is returned to atmospheric pressure under a cover of nitrogen at a temperature of 40° C.

Slow wall cooling is continued, at a constant rate from 40° C. to 10° C. over 3 hours.

The pyrocatechol crystals appear at 31° C. Seeding is not used in this example.

Maintenance of the temperature at 10° C. is performed for 30 minutes before filtration of the pyrocatechol suspension.

The suspension of crystalline pyrocatechol is then filtered on a flat filter maintained at a temperature of 10° C., under nitrogen, to obtain 688.0 g of wet pyrocatechol with a moisture content of 3.1% measured by the Karl Fischer method and 1312 g of mother liquors ($F_{17}$).

The solution of mother liquors ($F_{17}$) is stored for subsequent treatment.

The wet pyrocatechol is dried in an oven under reduced pressure (100 mbar) and under a stream of nitrogen, at 90° C., for 4 hours with removal of 15.6 g of water ($F_{18}$).

672.4 g of pyrocatechol $PC^6$ are isolated, the mass composition of which, determined by high-performance liquid chromatography and expressed relative to an anhydrous product, is as follows:
  pyrocatechol content: 99.94%
  dihydroxybenzoquinone content: 380 ppm
  hydroquinone content: <65 ppm
  content of phenolic compounds: 155 ppm
  The crystallization yield is 67%.
  The physical characteristics of the pyrocatechol $PC^6$ are as follows:
  diameter $d_{0.1}$: 57 μm
  median diameter $d_{0.5}$: 328 μm
  diameter $d_{0.9}$: 732 μm
  $CV = (d_{0.9} - d_{0.1})/2d_{0.5}$: 1.03
  bulk mass per unit volume: 0.610 g/cm³
  tamped mass per unit volume: 0.670 g/cm³
  compressibility index: 0.08
  flowability index $ff_{c.inst.}$: 20

Example 7

This example is a variant of Example 5 with additional water washing of the pyrocatechol crystals.

A sequence of tests of the type of those of Example 1 is performed: tests $N_{(i)}$ with $_{(i)} = 1$ to 10.

The mother liquors ($F_{20}$) and washing liquors ($F_{21}$) of test $N_{(0)}$ are 90% recycled into the crystallizing basin feed for test $N_{(1)}$ and so on for the following tests.

The remainder of the charge for each test is the crude pyrocatechol charge and a remainder, or a removal of water by evaporation ($F_{23}$), to maintain a pyrocatechol concentration of 60% by mass in the medium to be crystallized.

The total charge of the crystallization apparatus is maintained at 2500 g.

This series of tests $N_{(1)}$ to $N_{(10)}$ simulates the achieval of a pseudostationary state of equilibrium for a continuous crystallization process with partial recycling of the mother liquors.

The conditions of tests $N_{(10)}$ are described hereinbelow.

A total charge of 2500 g of constituents formed from demineralized water and mother liquors and washing liquors recycled from test $N_{(9)}$ at room temperature and the remainder of crude pyrocatechol whose mass % composition is as follows: 99.843% of pyrocatechol, 0.112% of dihydroxybenzoquinone, 0.0055% of hydroquinone, 0.0385% of phenolic compounds, to obtain a pyrocatechol concentration of 60% by mass, is introduced into a jacketed stirred crystallizing basin with a working volume of 2.5 liters, stirred with a three-paddle stirring rotor with axial output and variable speed, equipped with 4 90° counterpaddles, fitted with a condenser and maintained under nitrogen and at a jacket temperature of 55° C.

The overall content of impurities in the mixture to be crystallized, relative to the pyrocatechol present, is 1.5% by mass, and the corresponding pyrocatechol purity is 98.5% by mass.

Total dissolution of the pyrocatechol is achieved with stirring for about 30 minutes; maintenance of the temperature of the medium at 50° C. is performed for 10 minutes.

Rapid cooling over 15 minutes from 50° C. to 39° C. is then performed.

Seeding with 2 g of crystals (screen cutoff of between 125 and 160 microns) of purified pyrocatechol initiates the crystallization at 38.2° C.

Slow cooling at constant rate from 39° C. to 5° C. over 5 hours is then performed.

The suspension of crystalline pyrocatechol is then filtered on a flat filter maintained at a temperature of 5° C., with stirring, to obtain 1380.7 g of wet pyrocatechol with a moisture content of 4.0% measured by the Karl Fischer method and 1121.3 g of mother liquors ($F_{20}$).

The solution of mother liquors ($F_{20}$) is stored for subsequent treatment.

The wet pyrocatechol cake is washed with 165.4 g of demineralized water at 5° C. (washing proportion of 3/1 expressed as kg of washing water/kg of mother liquors impregnating the wet cake) on the filter.

After filtration, an equivalent filtrate of washing liquor ($F_{21}$) is recovered.

The mother liquors ($F_{20}$) and washing liquors ($F_{21}$) are mixed together after partial purging of the mother liquors ($P_6$) and concentrated by evaporation of a stream of condensates ($F_{23}$) for subsequent recycling.

The wet pyrocatechol is dried in an oven under reduced pressure (100 mbar) and under a stream of nitrogen, at 90° C., for 6 hours with removal of 52.8 g of water ($F_{22}$).

1327.9 g of pyrocatechol $PC^7$ are isolated, the mass composition of which, determined by high-performance liquid chromatography and expressed relative to an anhydrous product, is as follows:

pyrocatechol content: 99.9795%
dihydroxybenzoquinone content: 140 ppm
hydroquinone content: <10 ppm
content of phenolic compounds: 55 ppm
The crystallization yield is 89%.
The physical characteristics of the pyrocatechol $PC^7$ are as follows:
Laser Granulometry
diameter $d_{0.1}$: 55 µm
median diameter $d_{0.5}$: 350 µm
diameter $d_{0.9}$: 725
CV = $(d_{0.9} - d_{0.1})/2d_{0.5}$: 0.96
bulk mass per unit volume: 0.670 g/cm³
tamped mass per unit volume: 0.705 g/cm³
compressibility index: 0.05
flowability index $ff_{c.inst.}$: 23

By way of comparison, the results of particle size analyses performed by screening on a sample of pyrocatechol crystals $PC^7$, a sample of crude pyrocatechol (flakes) and a commercial solid form, and also the other properties, are presented.

TABLE I

| | Example reference | | |
|---|---|---|---|
| | 7A | 7B | 7C |
| | Physical characteristics | | |
| Screen particle size | Pyrocatechol $PC^7$ Cumulative % passing by mass | Pyrocatechol flakes Cumulative % passing by mass | Commercial pyrocatechol in solid form Cumulative % passing by mass |
| 100 µm | 1.2% | 5.9% | 5.5% |
| 200 µm | 6.0% | 8.8% | 16.4% |
| 315 µm | 26.3% | 11.2% | 26.5% |
| 500 µm | 69.3% | 13.1% | 31.8% |
| 800 µm | 93.0% | 15.5% | 34.0% |
| 1000 µm | 100% | 46.7% | 64.0% |
| 2500 µm | 100% | 89.2% | 98.0% |
| 5000 µm | 100% | 100% | 100% |
| Bulk mass per unit volume (g/cm³) | 670 | 630 | 728 |
| Tamped mass per unit volume (g/cm³) | 705 | 716 | 831 |
| Compressibility index | 0.05 | 0.12 | 0.12 |
| Flowability index $ff_{c.inst.}$ | 23 | 11 | 5.9 |

FIG. 9 corresponds to a photograph taken using a digital camera, which represents the morphology of the pyrocatechol crystals in the form of a crystalline powder described in Example 7A (invention).

FIG. 11 corresponds to a photograph taken using a digital camera, which represents the morphology of a commercially available solid form described in Example 7C.

Figure 1:
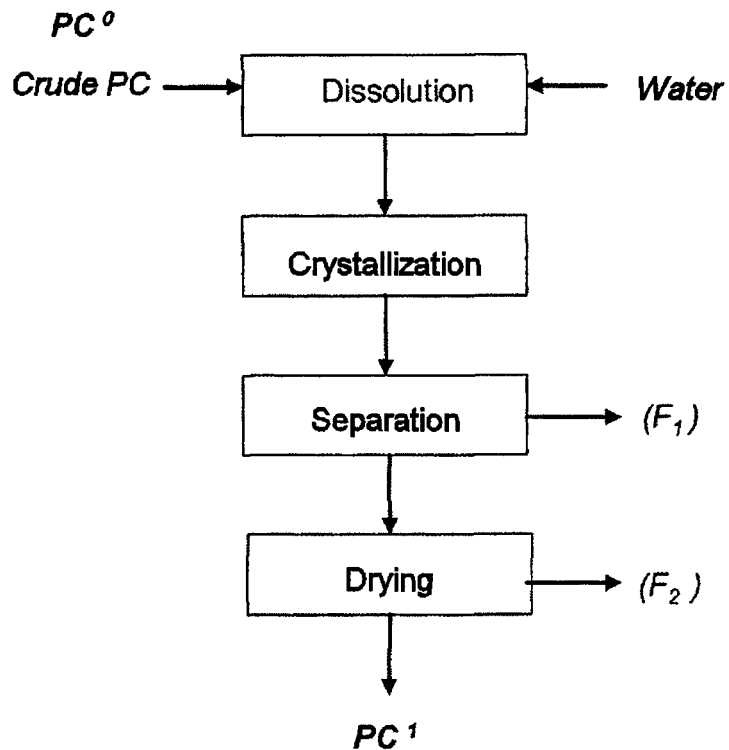

It should be noted that the particle size distribution of the pyrocatechol of the invention is different from that of the other two pyrocatechols.

Example 8

This example is a variant of Example 6, with additional washing with water of the pyrocatechol crystals.

A sequence of tests of the type of those in Example 1 is performed: tests $N_{(i)}$ with $_{(i)}$ = 1 to 10.

The mother liquors ($F_{25}$) and washing liquors ($F_{26}$) of test $N_{(0)}$ are 90% recycled into the crystallizing basin feed for test $N_{(1)}$ and so on for the following tests.

The remainder of the charge for each test is the crude pyrocatechol charge and a remainder, or a removal of water by evaporation ($F_{28}$), to maintain a pyrocatechol concentration of 50% by mass in the medium to be crystallized.

The total charge to the crystallization apparatus is maintained at 2500 g.

This series of tests $N_{(1)}$ to $N_{(10)}$ simulates the achieval of a pseudostationary state of equilibrium for a continuous crystallization process with partial recycling of the mother liquors.

The conditions of test $N_{(10)}$ are described hereinbelow.

A total charge of 2500 g of constituents formed from demineralized water and mother liquors and washing liquors recycled from test $N_{(9)}$ at room temperature and the remainder of crude pyrocatechol whose mass % composition is as follows: 99.843% of pyrocatechol, 0.112% of dihydroxybenzoquinone, 0.0055% of hydroquinone, 0.0385% of phenolic compounds, to obtain a pyrocatechol concentration of 50% by mass, is introduced into a jacketed stirred crystallizing basin with a working volume of 2.5 liters, stirred with a three-paddle stirring rotor with axial output and variable speed, equipped with 4 90° counterpaddles, fitted with a condenser and maintained under nitrogen and at a jacket temperature of 55° C.

The overall content of impurities in the mixture to be crystallized, relative to the pyrocatechol present, is 1.5% by mass, and the corresponding pyrocatechol purity is 98.5% by mass.

Total dissolution of the pyrocatechol is achieved with stirring for about 30 minutes; maintenance of the temperature of the medium at 50° C. is performed for 10 minutes.

A fraction of condensates of water vapor of 500 g ($F_{24}$) is withdrawn, bringing the pyrocatechol concentration to 50% by mass in the mixture, by placing the crystallizing basin under a variable reduced pressure between 1010 mbar and 750 mbar and maintaining the boiling at 95° C.

Rapid cooling over 60 minutes from 95° C. to 40° C. is then performed by combining cooling by evaporation (with total recycling of the condensates) and wall cooling.

The crystallizing basin is returned to atmospheric pressure under a cover of nitrogen at a temperature of 40° C.

Slow wall cooling is continued, at a constant rate from 40° C. to 10° C. over 3 hours. The pyrocatechol crystals appear at 31° C. Seeding is not used in this example.

Maintenance of the temperature at 10° C. is performed for 30 minutes before filtering the pyrocatechol suspension.

The suspension of crystalline pyrocatechol is then filtered on a flat filter maintained at a temperature of 10° C., under nitrogen, to obtain 690.8 g of wet pyrocatechol with a moisture content of 3.5% measured by the Karl Fischer method and 1309.2 g of mother liquors ($F_{25}$).

The solution of mother liquors ($F_{25}$) is stored for subsequent treatment.

The wet pyrocatechol cake is washed with 72.5 g of demineralized water at 10° C. (washing proportion of 3/1 expressed as kg of washing water/kg of mother liquors impregnating the wet cake) on the filter.

After filtration, an equivalent filtrate of washing liquors ($F_{26}$) is recovered.

The mother liquors ($F_{25}$) and washing liquors ($F_{26}$) are mixed together after partial purging of the mother liquors ($P_8$) and concentrated by evaporation of a stream of condensates ($F_{28}$) for subsequent recycling.

The wet pyrocatechol is dried in an oven under reduced pressure (100 mbar) and under a stream of nitrogen, at 90° C. for 6 hours with removal of 22.6 g of water ($F_{22}$).

668.2 g of pyrocatechol $PC^8$ are isolated, the mass composition of which, determined by high-performance liquid chromatography and expressed relative to an anhydrous product, is as follows:

pyrocatechol content: 99.9897% dihydroxybenzoquinone content: 74 ppm hydroquinone content: <10 ppm content of phenolic compounds: 20 ppm The crystallization yield is 67%.

The physical characteristics of the pyrocatechol $PC^7$ are as follows:

Laser Granulometry diameter $d_{0.1}$: 55 μm median diameter $d_{0.5}$: 345 μm diameter $d_{0.9}$: 735 μm $CV=(d_{0.9}-d_{0.1})/2d_{0.5}$: 0.99 bulk mass per unit volume: 0.675 g/cm$^3$ tamped mass per unit volume: 0.707 g/cm$^3$ compressibility index: 0.05 flowability index $ff_{c.inst.}$: 23

Example 9

This example is performed according to FIG. 1, by reproducing Example 1, with different conditions concerning the purity of the crude pyrocatechol, the concentration of the crude pyrocatechol in water and the crystallization end temperature, these conditions being specified in the following table, along with the purity and yield obtained:

TABLE II

| Ref. Ex. | Crude pyrocatechol purity (%) | Concentration of pyrocatechol in water (%) | Crystallization end temperature | Final purity obtained (%) | Purification yield (%) |
|---|---|---|---|---|---|
| 9 | 99.84 | 65 | 3° C. | 99.9944 | 91.0 |

Example 10

Figure 2:
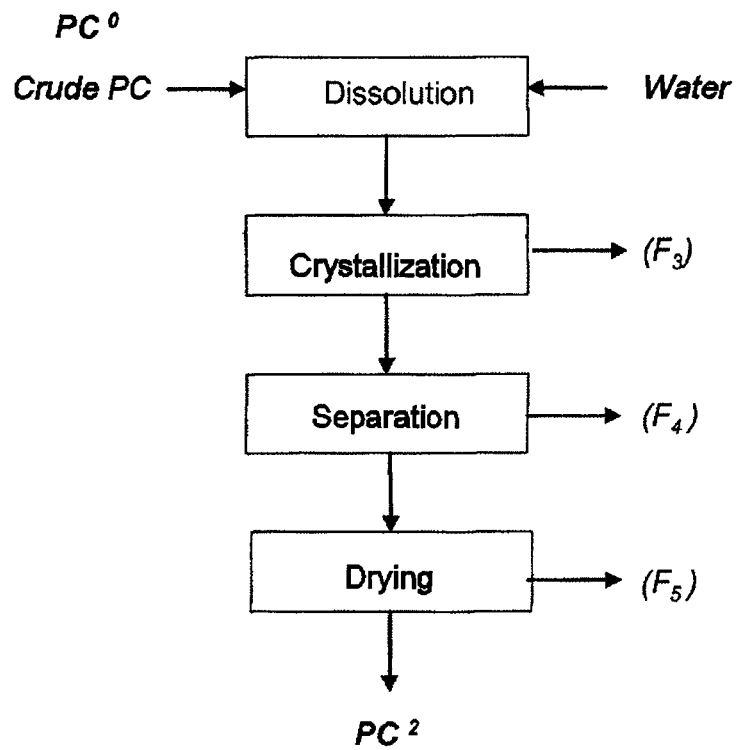
Figure 3:
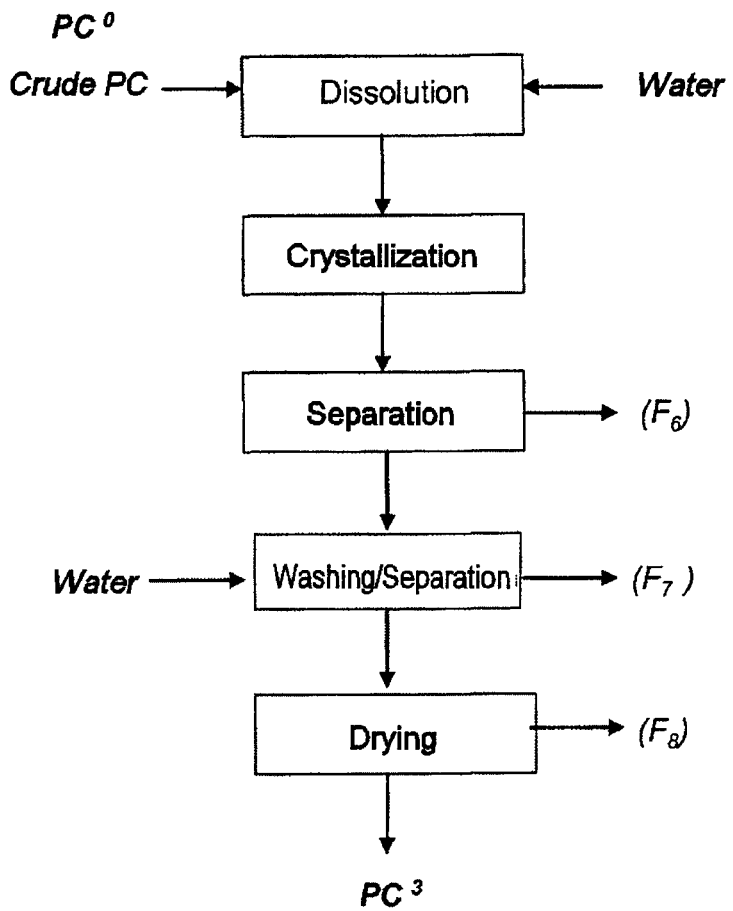
Figure 4:
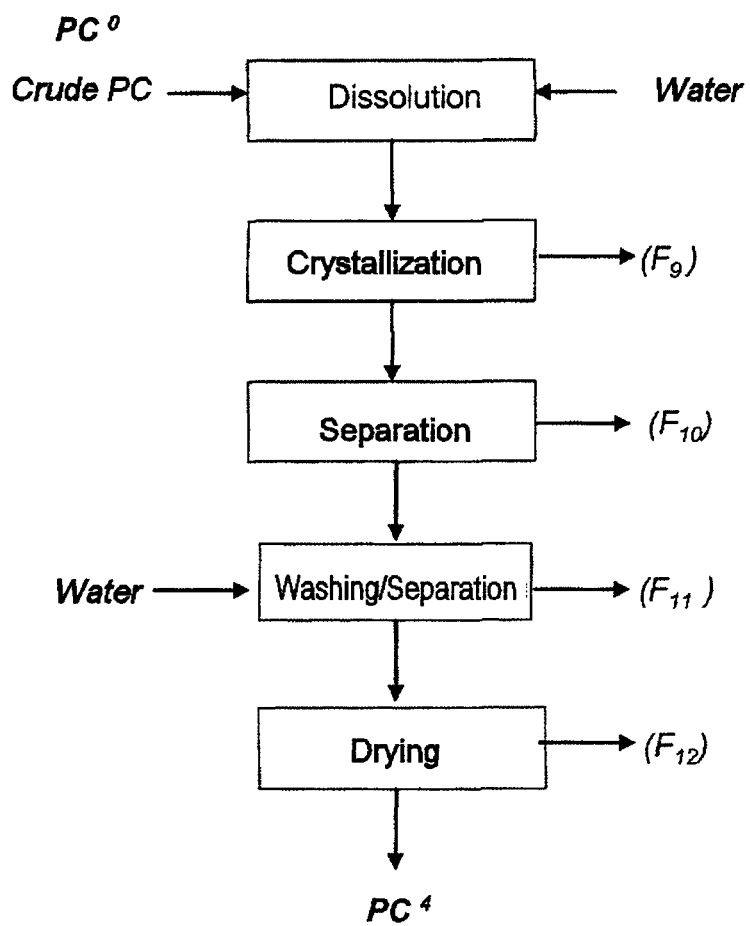
Figure 5:
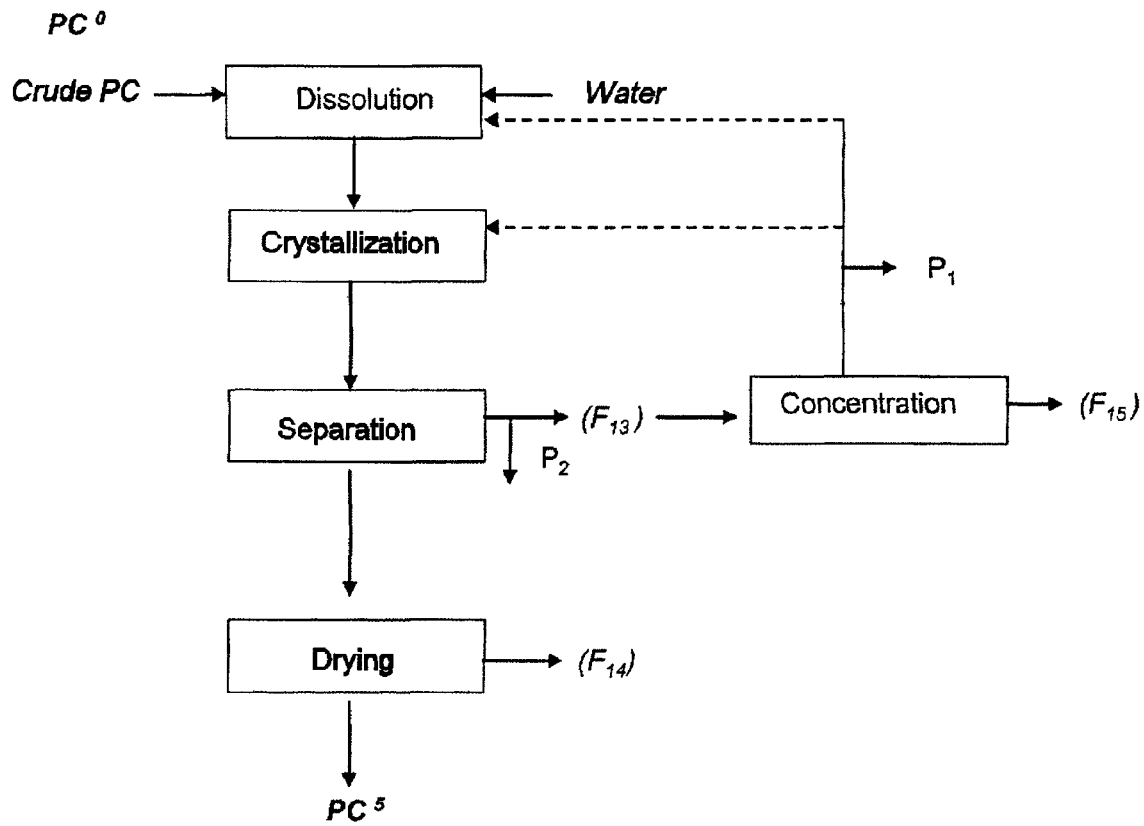
Figure 6:
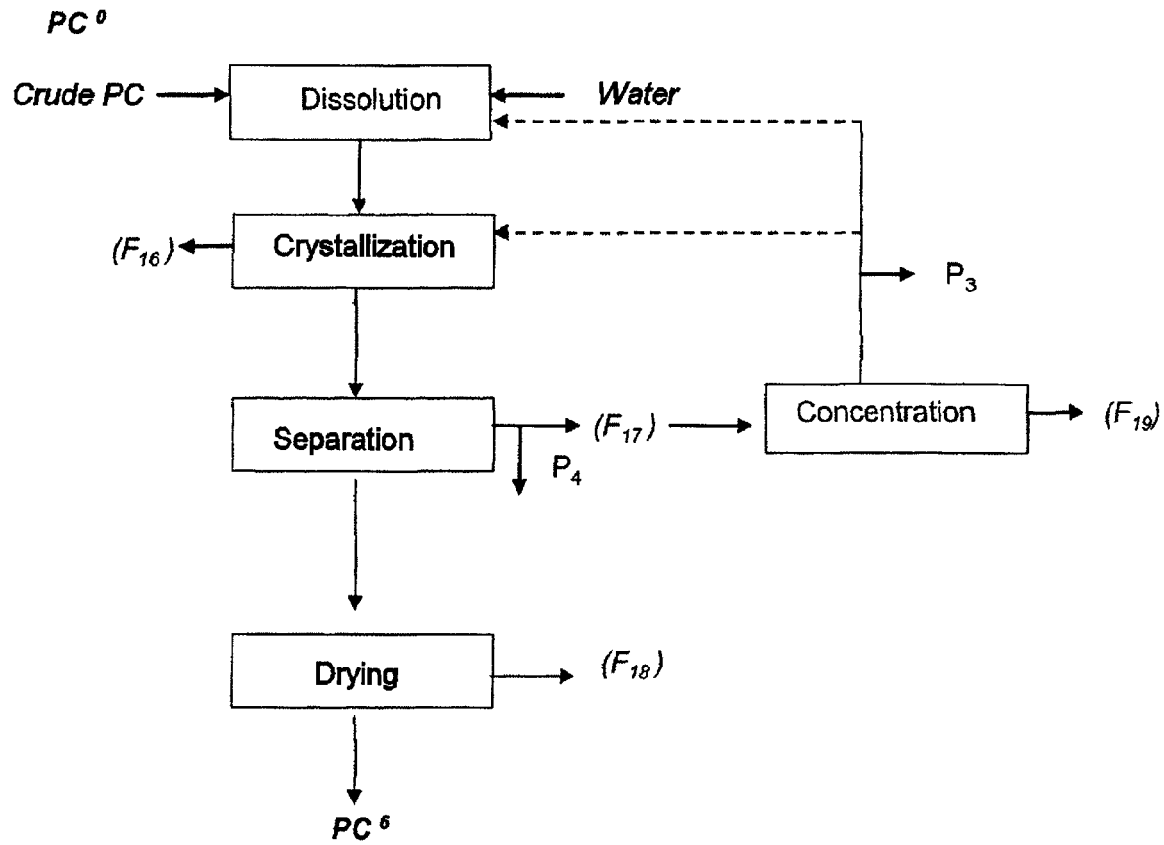
Figure 7:
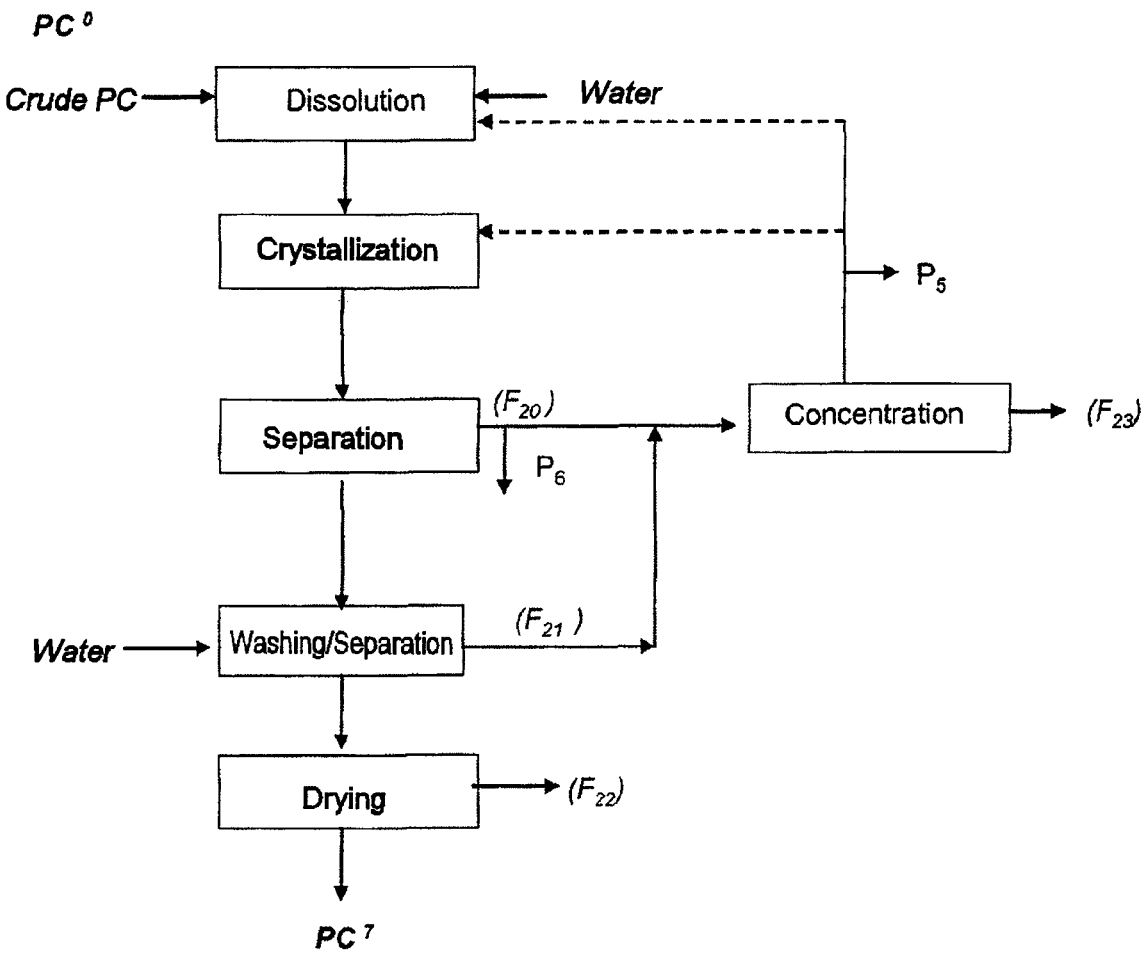
Figure 8:
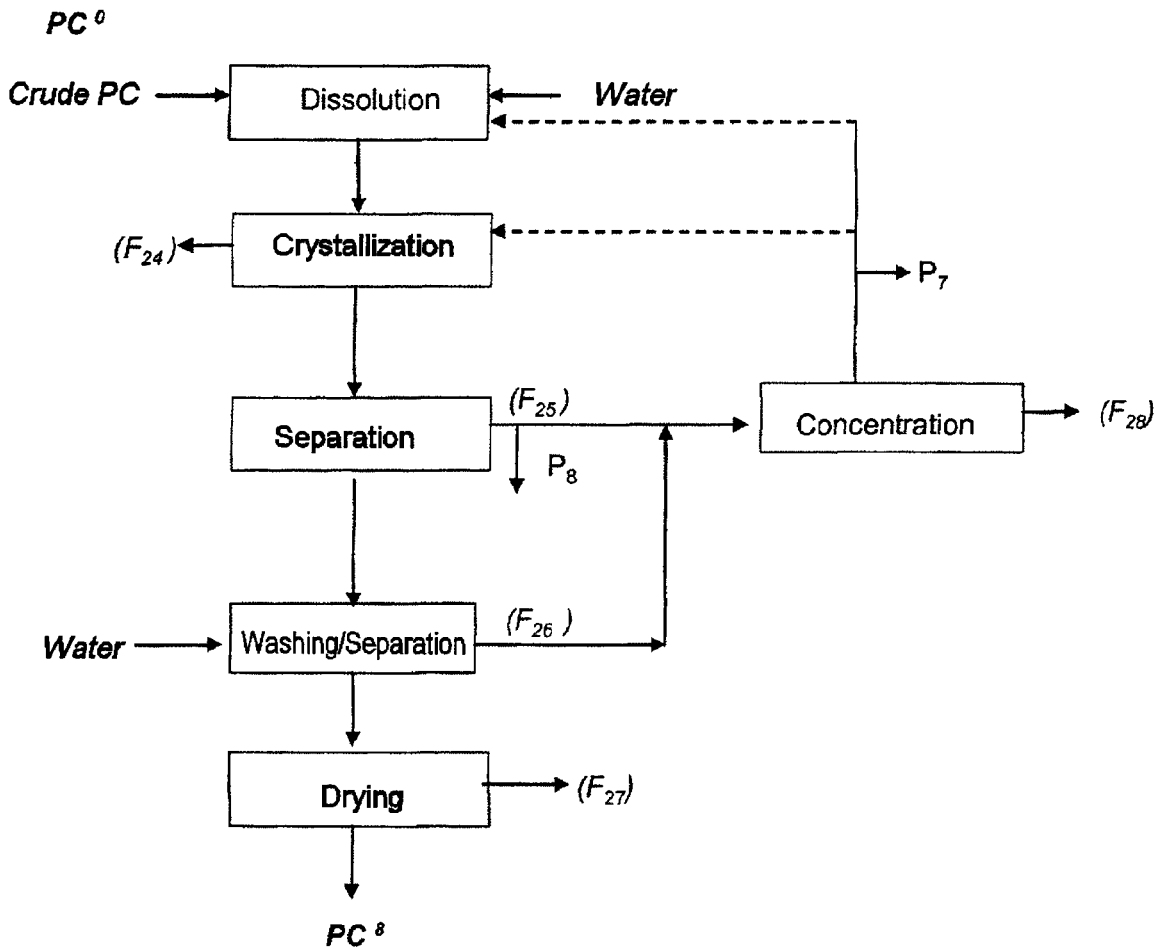
Figure 9:
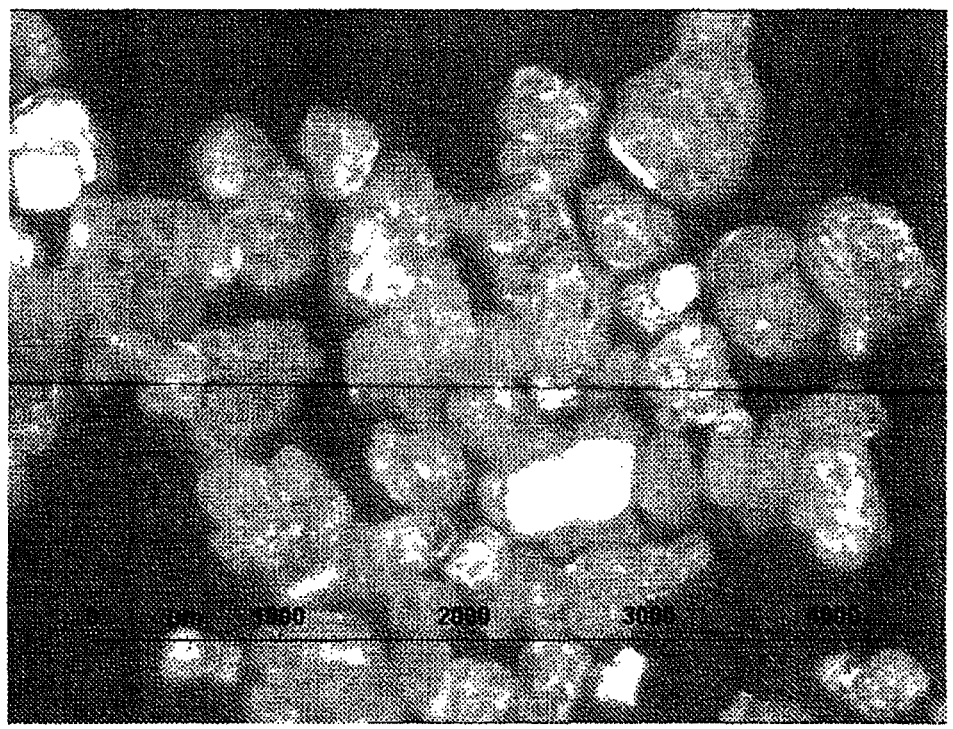
Figure 10:
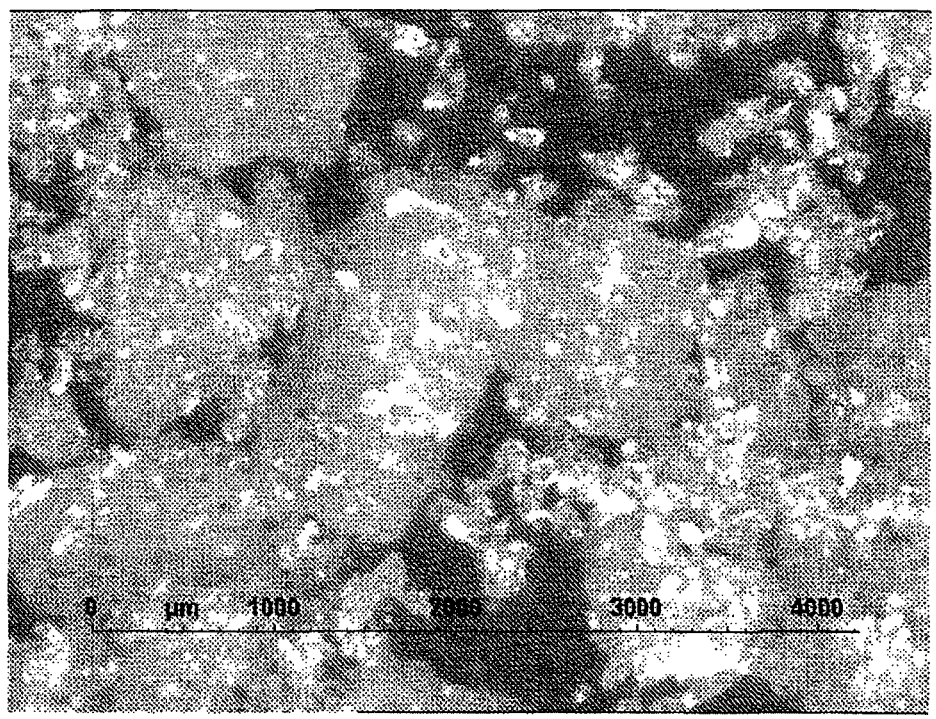
FIG. 10 represents a photograph taken using a digital camera, which shows the morphology of flake type of commercial pyrocatechol (Example 7B).
Figure 11:
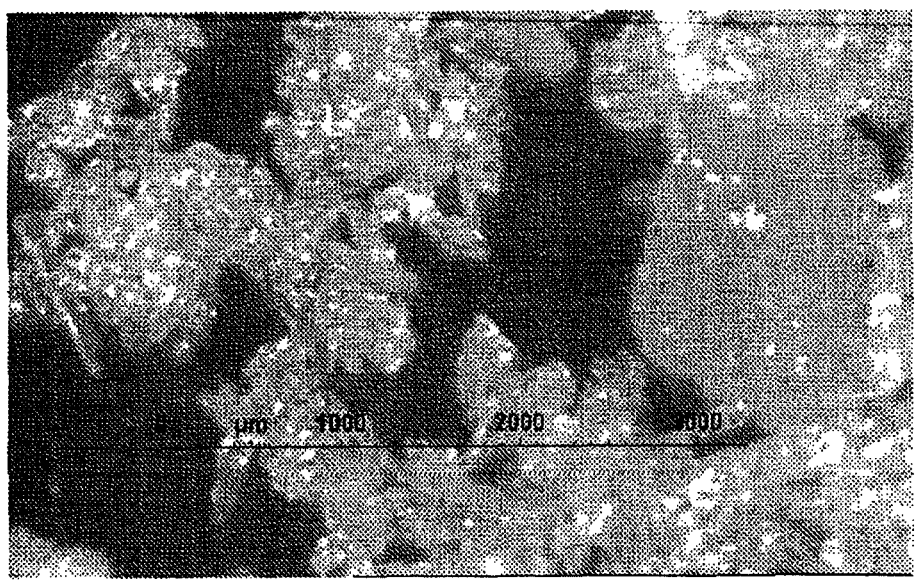
Figure 12:
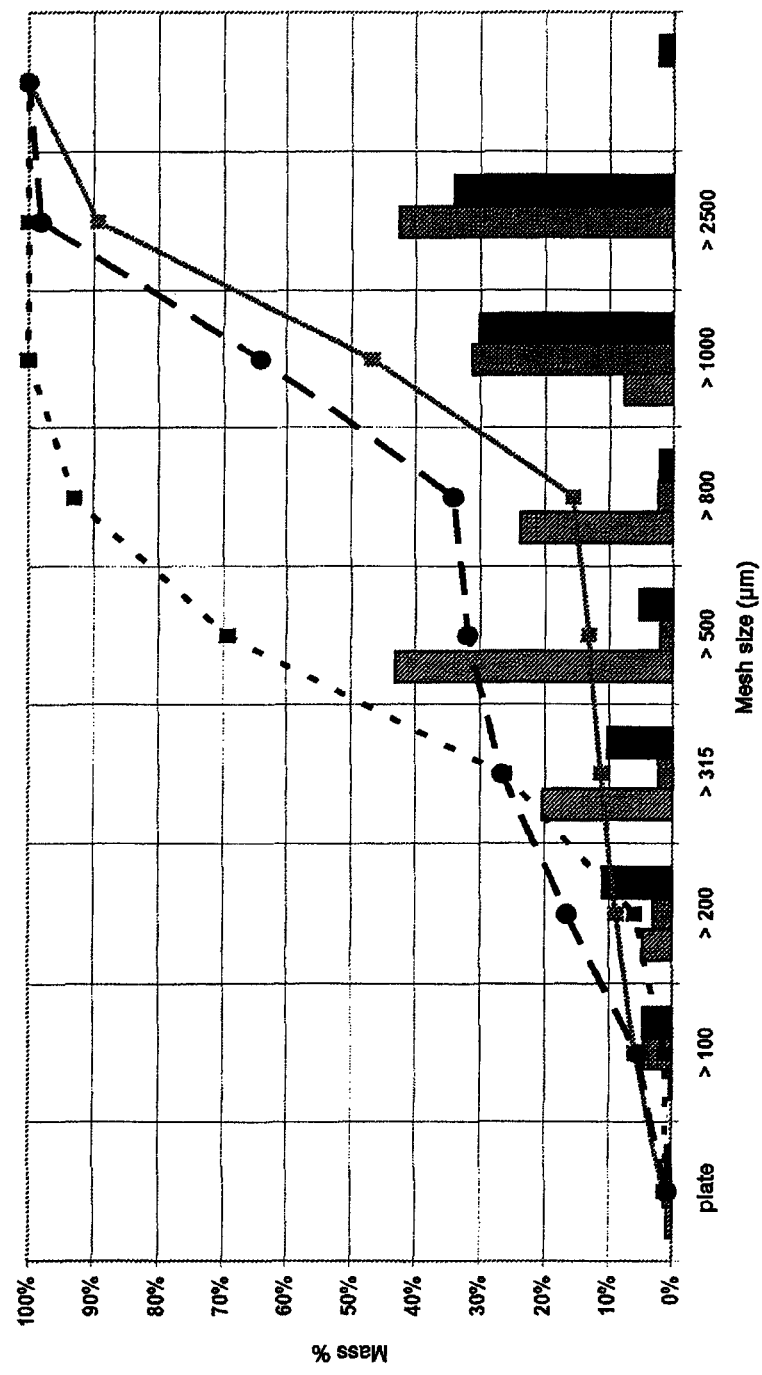
FIG. 12 is a graph demonstrating the particle size distribution obtained by screening of the pyrocatechol of the invention (short-dashed curve); of pyrocatechol in the form of flakes (solid-line curve); and of a commercial pyrocatechol in a solid form (long-dashed curve).

This example is performed according to FIG. 2, reproducing Example 2, under the conditions specified hereinbelow.

A crude pyrocatechol solution with a purity of 99.84% and having an initial concentration in water of 50% by mass is used at the start.

A concentration operation is performed in a crystallizing basin such that the pyrocatechol concentration becomes equal to 65% by mass.

The conditions and results are specified in the following table:

TABLE III

| Ref. Ex. | Crude pyrocatechol purity (%) | Concentration of pyrocatechol in water (%) | Crystallization end temperature | Final purity obtained (%) | Purification yield (%) |
|---|---|---|---|---|---|
| 10 | 99.84 | 65 | 1° C. | 99.9941 | 93.2 |

It should be clearly understood that the invention defined by the attached claims is not limited to the particular embodiments indicated in the above description, but encompasses the variants thereof which do not depart either from the scope or spirit of the present invention.

The invention claimed is:

1. A process for preparing purified pyrocatechol from a crude pyrocatechol comprising pyrocatechol, small amounts of impurities including dihydroxybenzoquinone, traces of hydroquinone, and phenolic compounds in a content of less than 5% by mass, comprising at least the following steps:
dissolving the crude pyrocatechol in water to a concentration ranging from 40% to 90% by mass;
crystallizing the pyrocatechol, by cooling to a temperature ranging from 0 to 20° C.;
separating the crystalline pyrocatechol from an aqueous phase formed from the crystallization mother liquors; and
optionally drying the purified pyrocatechol.

2. The process of claim 1, wherein the purified pyrocatechol is dried.

3. The process of claim 2, wherein the step of crystallizing the pyrocatechol comprises evaporation and outputting a stream of condensates.

4. The process of claim 2, further comprising washing the crystallized pyrocatechol with water and optionally collecting the washing liquors.

5. The process of claim 3, further comprising washing the crystallized pyrocatechol with water and optionally collecting the washing liquors.

6. The process of claim 1, further comprising the steps of:
recycling a stream comprising the aqueous phase formed from the crystallization mother liquors into the dissolving or crystallizing step;
optionally concentrating the stream; and
purging the stream, optionally after concentrating said stream.

7. The process of claim 6, wherein the step of crystallizing the pyrocatechol comprises evaporation and outputting a stream of condensates.

8. The process of claim 6, further comprising the step of:
washing the separated pyrocatechol with water and collecting washing liquors.

9. The process of claim 8, wherein the washing liquors are mixed with the aqueous phase formed from the crystallization mother liquors before said concentrating.

10. The process of claim 7, further comprising the step of:
washing the separated pyrocatechol with water and collecting washing liquors.

11. The process of claim 10, wherein the washing liquors are mixed with the aqueous phase formed from the crystallization mother liquors before said concentrating.

12. The process of claim 1, wherein said crude pyrocatechol is dissolved in water to a concentration ranging from 50% to 90% by mass.

13. The process of claim 1, wherein the dissolving step is performed at a temperature ranging from 40° C. to 100° C.

14. The process of claim 1, wherein crystallization the pyrocatechol is performed by cooling from the dissolution temperature to a temperature ranging from 0 to 10° C.

15. The process of claim 1, wherein crystallization seeds are introduced in an amount less than 2% by mass relative to the mass of pyrocatechol crystals to be obtained.

16. The process of claim 2, wherein the pyrocatechol is dried at a drying temperature ranging from 50° C. to 100° C.

17. The process of claim 3, wherein the evaporation is performed before or during the crystallization and comprises heating at atmospheric pressure or under a reduced pressure ranging from 25 mbar to 1 bar, at a temperature ranging from 25° C. to 100° C.

18. The process of claim 5, wherein the mass ratio of washing water to mother liquors comprising the moisture content of the pyrocatechol is not more than 3.

19. The process of claim 6, comprising concentrating the recycled stream to an amount of pyrocatechol ranging from 10% to 90% by mass.

20. The process of claim 19, wherein concentrating the recycled stream comprises heating said stream at atmospheric pressure or under a reduced pressure, at a temperature ranging from 70° C. to 100° C.

21. The process of claim 1, further comprising a step of treating the crude pyrocatechol in water with carbon black or active charcoal before the crystallizing step, wherein said carbon black or active charcoal is optionally separated from the pyrocatechol after said treatment.

22. The process of claim 1, wherein one or more steps are performed under an atmosphere of inert gas.

23. The process of claim 1, wherein the crude pyrocatechol comprises impurities in an amount ranging from 0.1% to 2.5% by mass relative to the total mass of the crude pyrocatechol.

24. The process of claim 1, wherein the mass ratio of the dihydroxybenzoquinone to the sum of the impurities ranges from 0.5 to 0.8.

25. The process of claim 1, wherein the mass ratio of the phenolic compounds to the sum of the impurities ranges from 0.18 to 0.4.

26. The process of claim 1, wherein the mass ratio of the hydroquinone to the sum of the impurities ranges from 0.2 to 0.10.

27. The process of claim 1, wherein the crude pyrocatechol comprises, by mass relative to the total amount of crude pyrocatechol:
from 97.5% to 99.9% of pyrocatechol,
from 0.003% to 0.07% of hydroquinone,
from 0.02% to 0.5% of phenolic compounds, and
from 0.07% to 1.5% of hydroxybenzoquinone.

28. The process of claim 1, wherein the crude pyrocatechol is obtainable from a hydroxylation reaction of phenol with hydrogen peroxide in the presence of an acid catalyst followed by distillation of said mixture.

29. The process of claim 28, wherein said pyrocatechol is obtainable from a distillation head and a mixture consisting essentially of hydroquinone with a small amount of impurities is obtainable from a distillation tail.

30. The process of claim 1, wherein said purified pyrocatechol has a purity ranging from 99% to 99.995%.

31. The process of claim 1, wherein said purified pyrocatechol has a purity ranging from 99.5% to 99.99%.

32. The process of claim 30, wherein a said purified pyrocatechol comprises less than 10 ppm of hydroquinone, 40 ppm of dihydroxybenzoquinone, and 40 ppm of phenolic compounds.

* * * * *

UNITED STATES PATENT AND TRADEMARK OFFICE
CERTIFICATE OF CORRECTION

PATENT NO.        : 8,628,849 B2
APPLICATION NO. : 12/809318
DATED             : January 14, 2014
INVENTOR(S)       : Jean-Claude Masson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 684 days.

Signed and Sealed this

Twenty-second Day of September, 2015

Michelle K. Lee
*Director of the United States Patent and Trademark Office*